US007005129B1

(12) United States Patent
Apicella et al.

(10) Patent No.: US 7,005,129 B1
(45) Date of Patent: *Feb. 28, 2006

(54) NON-TOXIC MUTANTS OF PATHOGENIC GRAM-NEGATIVE BACTERIA

(75) Inventors: Michael A. Apicella, Solon, IA (US); Melvin G. Sunshine, Iowa City, IA (US); Na-Gyong Lee, Incheon (KR); Bradford W. Gibson, Berkeley, CA (US); Rasappa Arumugham, Pittsford, NY (US)

(73) Assignees: University of Iowa Research Foundation, Iowa City, IA (US); The Regents of the University of California, Oakland, CA (US)

(*) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/077,572

(22) PCT Filed: Nov. 27, 1996

(86) PCT No.: PCT/US96/18984

§ 371 (c)(1),
(2), (4) Date: Oct. 13, 1998

(87) PCT Pub. No.: WO97/19688

PCT Pub. Date: Jun. 5, 1997

Related U.S. Application Data

(63) Continuation-in-part of application No. 08/565,943, filed on Dec. 1, 1995, now Pat. No. 6,887,483.

(51) Int. Cl.
*A61K 39/385* (2006.01)
*A61K 39/02* (2006.01)
*A61K 39/102* (2006.01)
*C07H 1/00* (2006.01)
*G01N 33/53* (2006.01)

(52) U.S. Cl. .............................. 424/197.11; 424/234.1; 424/256.1; 424/193.1; 424/831; 424/184.1; 435/547; 536/127.1; 536/123.1

(58) Field of Classification Search ............ 424/236.1, 424/9.2, 184.1, 234.1, 93.1, 93.2, 93.4, 93.48, 424/282.1, 193.1, 197.11, 256.1, 831; 435/69.1, 435/69.3, 101, 172.1, 172.3, 243, 252.3, 435/547; 536/123.1; 530/390.1
See application file for complete search history.

(56) References Cited

U.S. PATENT DOCUMENTS

| 4,912,094 A | 3/1990 | Myers et al. ............. 514/54 |
| 4,929,604 A | 5/1990 | Munford et al. ......... 514/53 |
| 5,200,184 A | 4/1993 | Munford et al. ......... 424/94.61 |
| 5,641,492 A * | 6/1997 | Sprouse et al. .......... 424/258.1 |
| 6,482,807 B1 * | 11/2002 | Van Der Ley et al. ..... 514/54 |
| 6,548,287 B1 * | 4/2003 | Powell et al. ............ 435/243 |

FOREIGN PATENT DOCUMENTS

WO    WO-97/18837    5/1997

OTHER PUBLICATIONS

Gupta et al. Infect. Immun. 60: 3201-3208, 1992.*
Karow et al. Mol. Microbiol. 5: 2285-2292, 1991.*
Westphal et al. Methods in Carbohydrate Chemistry 5: 83-91, 1965.*
McLaughlin et al. J. Bacteriol. 174: 6455-6459, 1992.*
Karow ML. Molecular Genetics of the *Escherichia coli* htrB gnee. Ph.D. Dissertation, The Utah University, 1992.*
Jachymek W. Post Hih. Med. Dosw. 49: 171-178, 1995.*
Raetz CRH. Annu. Rev. Biochem. 59: 129-170, 1990.*
Kulshin et al. J. Bacteriol. 174: 1793-1800, 1992.*
Karow, M., et al., "Isolation and Characterization of the *Escherichia coli* htrB gene, whose product is essential for bacterial viability above 33degreesC in rich media", *Journal of Bacteriology*, vol. 173, No. 2, pp. 741-750, (Jan. 1991).
Karow, M., et al., "The lethal Phenotype 'caused by null mutations in the *Escherichia coli* htrB gene is suppressed by Mutations in the accBC Operon, Encoding two subunits of acetyl coenzyme A carboxylase", *Journal of Bacteriology*, vol. 174, No. 22, pp. 7407-7418, (Nov. 1992).
Lee, N., et al., "Mutation of the htrB locus of *Haemophilus influenzae* nontypable strain 2019 is associated with modifications of lipid A and physophorylation of the lipo-oligosaccharide", *The Journal of Biological Chemistry*, vol. 270, No. 45, pp. 27151-27159, (Nov. 10, 1995).
Lehmann, V., et al., "Isolation of a mutant from *Salmonella typhimurium* producing acyl-deficient lipopolysaccharides", 459-464, (1988).
Brooks, G.F., et al., "Enteric Gram-negative rods (enterobacteriaceae)", *Medical Microbiology*, p. 206, (1995).

(Continued)

Primary Examiner—S. Devi
(74) Attorney, Agent, or Firm—Viksnins Harris & Padys PLLP

(57) ABSTRACT

A method is provided for identifying, isolating, and producing htrB mutants of gram-negative bacterial pathogens. The method comprises mutating the htrB gene of a gram-negative bacterial pathogen so that there is a lack of a functional htrB protein, resulting in a mutant that lacks one or more secondary acyl chains contained in the wild type gram-negative bacterial pathogen, and displays substantially reduced toxicity as compared to the wild type strain. Also, the present invention provides methods for using a vaccine formulation containing the htrB mutant, the endotoxin isolated therefrom, or the endotoxin isolated therefrom which is then conjugated to a carrier protein, to immunize an individual against infections caused by gram-negative bacterial pathogens by administering a prophylactically effective amount of the vaccine formulation.

3 Claims, 7 Drawing Sheets

OTHER PUBLICATIONS

Lee, Na-Gyong., et al. ,"Mutation of the htrB Locus of *Haemophilus influenzae* nontypable strain 2019 is associated with modifications of Lipid A and phosphorylation of the liip-oligosaccharide", *J. of Biological Chem., 270 (45)*, (Nov. 10, 1995), pp. 27151-27159.

Golenbock, Douglas.T. ,et al. ,"Lipid A-like molecules that antagonize the effects of endotoxins on human monocytes", *J. of Biological Chem., 266(29)*, (1991), pp. 19490-19498.

Raetz, Christian.R. ,"Bacterial endotoxins: extraordinary lipids that activate eucaryotic signal transduction", *J. of Bacteriology, 175 (18)*, (Sep. 1993), pp. 5745-5753.

Hitchcock, P. , et al., "Morphological Heterogeneity Among Salmonella Lipopolysaccharide Chemotypes in Silver-Stained Polyacrylamide Gels", *J. of Bacteriology*, vol. 154, No. 1(Apr. 1983), 269-277.

* cited by examiner

And/Or

Hexaacyl diphosphoryl-Lipid A

Heptaacyl diphosphoryl-Lipid A

Heptaacyl diphosphoryl-Lipid A

*htrB-*

Hexaacyl diphosphoryl-Lipid A

NON-TOXIC MUTANTS OF PATHOGENIC GRAM-NEGATIVE BACTERIA

This application is a National Stage filing under 35 U.S.C. 371 of PCT/US96/18984 filed on Nov. 27, 1996 and published in English as WO 97/19688 on Jun. 5, 1997, which is a continuation-in-part of U.S. Ser. No. 08/565,943 (pending) filed on Dec. 1, 1995 U.S. Pat. No. 6,887,483.

This invention has been made with government support under grant AI 24616 awarded by the National Institutes of Health. The government has certain rights in the invention.

FIELD OF THE INVENTION

The present invention relates to compositions comprising altered endotoxin (lipooligosaccharide (LOS); lipopolysaccharide (LPS)) of gram-negative bacterial pathogens. More particularly, the present invention relates to the making of a form of endotoxin, by a genetically engineered gram-negative pathogen, which lacks a substantially toxic lipid A portion. Also disclosed are prophylactic and therapeutic uses of the substantially detoxified endotoxin, and of mutant gram-negative bacteria producing the substantially detoxified endotoxin.

BACKGROUND OF THE INVENTION

Gram-negative bacteria have an outer membrane comprised of components including proteins, lipoproteins, phospholipids, and glycolipids. The glycolipids comprise primarily endotoxin-lipopolysaccharides (LPS) or lipooligosaccharides (LOS), depending on the genus of bacteria. LPS are molecules comprised of a) a lipid A portion which consists of a glucosamine disaccharide that is substituted with phosphate groups and long chain fatty acids in ester and amide linkages;

b) a core polysaccharide which is attached to lipid A by an eight carbon sugar, KDO (ketodeoxyoctonoate), and heptose, glucose, galactose, and N-acetylglucosamine; and c) an O-specific side chain comprised of repeating oligosaccharide units which, depending on the genera and species of bacteria, may contain mannose, galactose, D-glucose, N-acetylgalactosamine, N-acetylglucosamine, L-rhamnose, and a dideoxyhexose (abequose, colitose, tyvelose, paratose, trehalose). LOS has a similar structure as LPS, containing a lipid A portion and a complex carbohydrate structure, but differs in that it does not contain repeating O-side chains.

The major antigenic determinants of gram-negative bacteria are believed to reside in the carbohydrate structure of the O-specific side chain of LPS and the complex carbohydrate structure of LOS. These carbohydrate structures may vary for different species of the same genera of gram-negative bacteria by varying one or more of the sugar composition; the sequence of oligosaccharides; the linkage between the oligosaccharides; and substitutions/modifications of an oligosaccharide (particularly a terminal oligosaccharide).

LPS and LOS have been considered as bacterial components which have potential as vaccine immunogens because of the antigenic determinants ("epitopes") residing in their carbohydrate structures. However, the chemical nature of LPS and LOS prevent the use of these molecules in vaccine formulations; i.e., active immunization with LPS or LOS is unacceptable due to the inherent toxicity of the lipid A portion. The pathophysiologic effects induced (directly or indirectly) by lipid A of LPS or LOS in the bloodstream include fever; leucopenia; leucocytosis; the Shwartzman reaction; disseminated intravascular coagulation; abortion; and in larger doses, shock and death. Accordingly, there are no currently available vaccines which induce antibody responses to LPS or LOS epitopes.

As shown in FIG. 1, the lipid A portion of endotoxin generally comprises a hydrophilic backbone of glucosamine disaccharide which is either monophosphorylated or diphosphorylated (positions 1 and 4'); and which carries at least six molecules of ester- and amide-bound fatty acids. Four molecules of (R)-3-hydroxytetradecanoate (e.g. 3-hydroxymyristoyl or β-hyroxymyristic acid or β-OH) are linked directly to the lipid A backbone at positions 2, 3, 2', and 3'. Hydroxyl groups of two of the four molecules of β-OH are substituted with normal fatty acids (termed "secondary acyl chains", and including dodecanoate, tetradecanoate, and hexadecanoate) in forming acyloxyacyl groups.

One approach to making a detoxified endotoxin molecule involves isolating the endotoxin, and enzymatically-treating the isolated endotoxin with a human neutrophilic acyloxyacyl hydrolase (U.S. Pat. Nos. 4,929,604, 5,013,661 and 5,200,184). The acyloxyacyl hydrolase hydrolyzes the fatty acids (non-hydroxylated, secondary acyl chains) from their ester linkages to hydroxy groups of β-OH (hydroxylated). The resultant altered endotoxin, from enzymatic treatment, contained a lipid A moiety lacking non-hydroxylated fatty acids. This altered endotoxin exhibited reduced in vivo toxicity, but retained antigenicity.

Another approach involves a method of modifying isolated endotoxin by selectively removing the β-OH that is ester-linked to the reducing-end glucosamine backbone at position 3 (U.S. Pat. No. 4,912,094; Reexamination B14, 912,094). The selective removal of β-OH was accomplished using alkaline hydrolysis. The resultant modified endotoxin exhibited reduced in vivo toxicity, but retained antigenicity.

Both approaches involve chemically treating isolated endotoxin. Neither approach discloses the production in a gram negative bacterial pathogen of an endotoxin having substantially reduced toxicity, yet retaining antigenicity. Further, there has been no disclosure of the use of a gram-negative bacteria, which has been engineered to produce an endotoxin having substantially reduced toxicity and yet retaining antigenicity, in a prophylactic or therapeutic vaccine against endotoxic shock and gram-negative bacteremia.

SUMMARY OF THE INVENTION

The present invention is directed to a method for producing, in a mutant gram-negative pathogen, LPS or LOS which exhibits substantially reduced toxicity as compared to the wild type endotoxin, and which retains the antigenicity of its corresponding wild type endotoxin. The method comprises creating a mutation in the htrB gene of the gram-negative bacterial pathogen such that there is a lack of functional HtrB protein in the mutated gram-negative bacterial pathogen. It was found that lipid A produced by the htrB mutant lacks one or both of the fatty acids (non-hydroxylated or secondary acyl chains) thereby rendering the endotoxin in an isolated form, or the mutant gram-negative bacterial pathogen bearing the endotoxin, substantially reduced in toxicity and yet retaining antigenicity, as compared to wild type. Endotoxin isolated from htrB mutants, or the htrB mutants themselves (whole cell vaccine), can be used to immunize individuals at risk of gram-negative bacteremia by inducing antibodies to the major antigenic determinants which reside in the carbohydrate structure of the O-specific side chain of LPS and the complex carbohydrate structure of LOS. Further, the htrB mutants can be engineered to express heterologous antigens of other microbial pathogens at the surface of the htrB mutant for presentation to a vaccinated individual's immune system in a multivalent vaccine. Also, the endotoxin isolated from the htrB mutants of the present invention may be used to generate LPS or LOS-specific antibody which may be useful for passive immunization and as reagents for diagnostic assays directed to detecting the presence of gram-negative bacterial pathogens in clinical specimens.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a schematic representation of the general structure of lipid A of gram negative bacteria of the family Enterobacteriaceae.

FIG. 2A is a schematic representation of the general structure of a species of lipid A, from the LOS of an htrB mutant, comprising pentaacyl diphosporyl lipid A.

FIG. 2B is a schematic representation of the general structure of a species of lipid A, from the LOS of an htrB mutant, comprising tetraacyl diphosporyl lipid A.

FIG. 3 is a graph showing the relative toxicity of an htrB mutant (○, Δ) as compared to wild type bacteria (□) in a TNFα release assay.

FIG. 4 is a photograph showing human primary respiratory epithelial cells unstimulated (control), exposed to NTHi 2019 LOS, or exposed to htrB mutant B29 LOS, and reacted with either a fluorescent probe that hybridizes to TNFα mRNA (probe 1) or a fluorescent control probe (probe 2).

FIG. 5 is a graph showing mean titers of anti-LOS antibody against NTHI 2019 LOS (antigen coating) in ELISA from mice immunized with NTHi 2019 (Pool 595), htrB mutant B29 LOS (Pool 597), or htrB mutant B29 LOS conjugated to a carrier protein (Pool 606), with adjuvant.

FIG. 6 is a graph showing the mean titers of anti-LOS antibody against htrB mutant B29 LOS (antigen coating) in ELISA from mice immunized with NTHi 2019 (Pool 595), htrB mutant B29 LOS (Pool 597), or htrB mutant B29 LOS conjugated to a carrier protein (Pool 606), with adjuvant.

FIG. 7 is a schematic representation comparing the structures of wild type *Salmonella* lipid A and htrB mutant lipid A.

DETAILED DESCRIPTION OF THE INVENTION

Definitions:

"Endotoxin" is a term used herein for purposes of the specification and claims to refer to the LPS or LOS of gram-negative bacterial pathogens, wherein the endotoxin is either in a cell-associated or isolated form. "htrB endotoxin" and "htrB mutant endotoxin" refer to endotoxin isolated and purified from an gram-negative bacterial pathogen htrB mutant.

"vaccine candidate or vaccine antigen" is a term used herein for purposes of the specification and claims to refer to an endotoxin epitope having one or more of the following properties (a–d): (a) is immunogenic; (b) is surface-exposed (which can be shown by techniques known in the art including immunofluorescence assays, electron microscopy staining procedures, and by bactericidal assays); (c) induces antibody having bactericidal activity in the presence of complement and/or functions in immune clearance mechanisms; (d) induces antibody which neutralizes other functional activity of the epitope (immunogenicity, or toxicity, etc.).

"Gram-negative bacterial pathogen" is a term used herein for the purposes of the specification and claims to refer to one or more pathogenic (to humans or animals) bacterium of a genus and species including *Neisseria meningitidis, Neisseria gonorrhoeae, Haemophilus influenzae, Haemophilus* ducreyi, other *Haemophilus* species, *Moraxella catarrhalis, Campylobacter jejuni, Salmonella typhimurium*, other *Salmonella* species, *Shigella dysentariae*, and other *Shigella* species, and *Pseudomonas aeruginosa*. "Substantially reduced in toxicity" is a term used herein for the purposes of the specification and claims to refer to a reduction in bioactivity of at least 10 fold to 100 fold or more as compared to wild type endotoxin. "Carrier protein" is a term used herein for the purposes of the specification and claims to refer to a protein which is conjugated to the htrB mutant endotoxin. While the htrB mutant endotoxin appears to be immunogenic on its own, it is known in the art that conjugation to a carrier protein can facilitate immunogenicity. Proteins which may be utilized according to the invention include any protein which is safe for administration to mammals and which may serve as an immunologically effective carrier protein. In particular embodiments, cell surface proteins, membrane proteins, toxins and toxoids may be used. Criteria for safety would include absence of primary toxicity and minimal risk of allergic reaction. Diphtheria and tetanus toxoids fulfill these criteria; that is, suitably prepared they are non-toxic, and the incidence of allergic reactions is acceptably low. Although the risk of allergic reaction may be significant for adults, it is minimal for infants.

According to additional particular embodiments of the invention, appropriate carrier proteins include, but are not limited to *Salmonella* flagellin, *Haemophilus* pilin, *Pseudomonas* pili, *Pseudomonas* exotoxin, outer membrane proteins of *Haemophilus* (15 kDa, 28–30 kDa, and 40 kDa membrane proteins) or *N. meningitidis* or *N. gonorrheae, Escherichia coli* heat labile enterotoxin LTB, cholera toxin, pneumolysin of *S. pneumoniae*, and viral proteins including rotavirus VP7 and respiratory syncytial virus F and G proteins. Additionally, there are many carrier proteins known in the art including, but not limited to, keyhole limpet hemocyanin, bovine serum albumin, and diphtheria toxin cross-reactive mutant protein ("CRM"). Additionally, there are several methods known in the art for conjugating endotoxin to a carrier protein. Such methods may include, but are not limited to, the use of glutaraldehyde, or succinimidyl m-maleimidobenzoate, or 1-ethyl-3-(3-dimethyl-aminopropyl)carbodiimide, or by using bromoacetylated carrier protein (see, e.g. Robey et al., 1989*, Anal. Biochem.* 177: 373–377). Conjugation of htrB endotoxin to a carrier protein toxin may reduce toxicity of the carrier protein toxin, but residual toxicity may remain. Further detoxification may be accomplished by means known in the art such as employing formalin which reacts with free amino groups of the carrier protein toxin.

Alternatively, native carrier protein toxin may be detoxified with formalin to produce a conventional toxoid before conjugation to the htrB mutant endotoxin. However, the prior formalin treatment reduces the number of free amino groups available for reaction during the conjugation process. CRM have an advantage in that they have no inherent toxicity yet none of their amino groups are occupied by the formalin. In the case of CRM197, which is immunologically identical to native toxin, treatment with formalin (though there is no need to detoxify) greatly enhances the immunological response. It is thought that this is due to stabilization of the molecule against degradation by mechanisms of the body and/or aggregation by cross-linking (immunogenicity of particles increases with size). While tetanus and diphtheria toxins are desirable carrier proteins, there may be other candidate carrier proteins which may also be suitable. Such other candidates for carriers include toxins and proteins of pseudomonas, *staphylococcus, streptococcus*, pertussis, and *E. coli*.

Conjugation of endotoxin to carrier proteins can be performed by a variety of methods such as by direct conjugation to the carrier protein by cyanogen bromide, reductive amination, or by using bifunctional linkers. Such bifunctional linkers include, but are not limited to, N-hydroxy succinimide-based linkers cystamine, glutaraldehyde, and diamino hexane. htrB endotoxin is modified to contain sulfhydryl groups with the use of N-hydroxy succinimide-based linkers, or by the use of carbodiimide-mediated condensation of cystamine. The sulfhydryl-containing htrB endotoxin intermediates are then reacted to a carrier protein that has been derivatized with N hydroxy succinimidyl bromo acetate. Preferably, sulfhydryl groups are exposed on the conjugating htrB endotoxin for making a thiol linkage with the bromoacetylated carrier protein.

Figure 1:
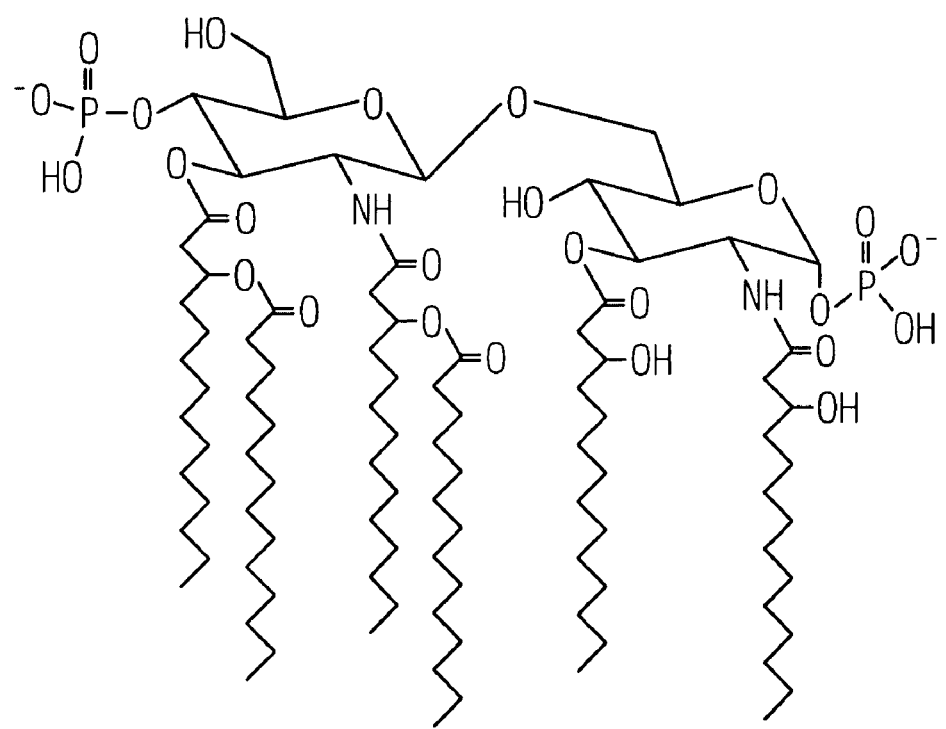

In a specific embodiment of the invention, htrB mutant endotoxin may be conjugated to a carrier protein, such as CRM, by using long chain sulfo N-succnimidyl 3-(2-pyridylthio)-propionate to thiolate the primary amino group(s) of the endotoxin. Long chain sulfo N-succnimidyl 3-(2-pyridylthio)-propionate was added to approximately 13 mg of the saccharide component of the htrB endotoxin in 0.1 M NaHCO$_3$ pH7.0 at a ratio of 1:1 (w/w) and incubated for an hour at room temperature. The mixture is then purified by gel filtration. The long chain sulfo N-succnimidyl 3-(2-pyridylthio)-propionate derivatized fractions were pooled. The N-pyridyl disulfides present in the derivatized fractions were reduced with 100 mM dithiothreitol, and purified by gel filtration. The thiolated endotoxin fractions were then collected. CRM197 was bromoacetylated by adding bromoacetic acid N hydroxy succinimide in a small volume of dimethyl formamide dropwise to CRM (in 0.1 M NaHCO$_3$) at a ratio of 1:1 (w/w) at 4° C. The solution was mixed and incubated for 1 hour at room temperature. The reaction mixture was then purified by gel filtration, and the fractions containing bromoacetylated protein were collected. Derivatization of amino groups on carrier protein to bromoacetyl groups was monitored by a decrease in the amount of free amino groups. Bromoacetyl CRM in 0.1 M NaHCO$_3$ was added to the thiolated htrB mutant endotoxin at a 1:1.5 ratio of protein to endotoxin (w/w) in 0.1 M NaHCO$_3$/1 mM EDTA, and the reaction was incubated overnight at 4° C. The final conjugate was then be purified by gel filtration in a phosphate buffered saline pH 6.9.

The methods and compositions of the present invention relate to LPS and LOS biosynthetic pathways of gram-negative bacterial pathogens. More specifically, the present invention relates to mutations in the htrB gene of gram-negative bacterial pathogens resulting in mutant bacteria bearing endotoxin which is substantially reduced in toxicity, and yet retains antigenicity, as compared to wild type bacteria of the same species.

The genetics of lipid A biosynthesis of enteric bacteria, as it was known at the time of the present invention, is summarized in Schnaitman and Klena (1993, *Microbiol. Rev.* 57:655–682). Genes 1pxA, 1pxB, 1pxC, and 1pxD encode gene products which function on the glucosamine backbone of lipid A including transfer of β-hydroxymyristic acid to glucosamine. The htrB gene was described as a gene that affects the inner core structure (KDO, heptose, phosphorylethanolamine (PEA)) which was discovered during a screen for genes necessary for growth of *Escherichia coli* at elevated temperatures. Knockout mutations of htrB resulted in mutant *E. coli* which exhibited a reduced sensitivity to deoxycholate, an inability to grow at temperatures above 32.5° C., and a decrease in LPS staining intensity (Schnaitman et al., 1993, supra; Karow et al., 1992, *J. Bacteriol.* 174:7407–7418). Karow et al. further noted that at between about 30° C. to about 42° C., *E. coli* htrB mutants have changes in the fatty acid composition of both LPS and phospholipids, and particularly, overproduce phospholipids, as compared to wild type. However, it was neither known nor suggested which one or more of the at least six molecules of ester- or amide bound fatty acids is lacking in the lipid A portion of LPS of htrB mutants. Also no mention was made that htrB mutants contained a lipid A moiety specifically lacking one or both non-hydroxylated (secondary acyl chain) fatty acids responsible for endotoxicity; i.e. that the htrB mutant contained an altered endotoxin exhibiting reduced in vivo toxicity, but retaining antigenicity ("htrB endotoxin"), as compared to wild type.

Figure 2A:
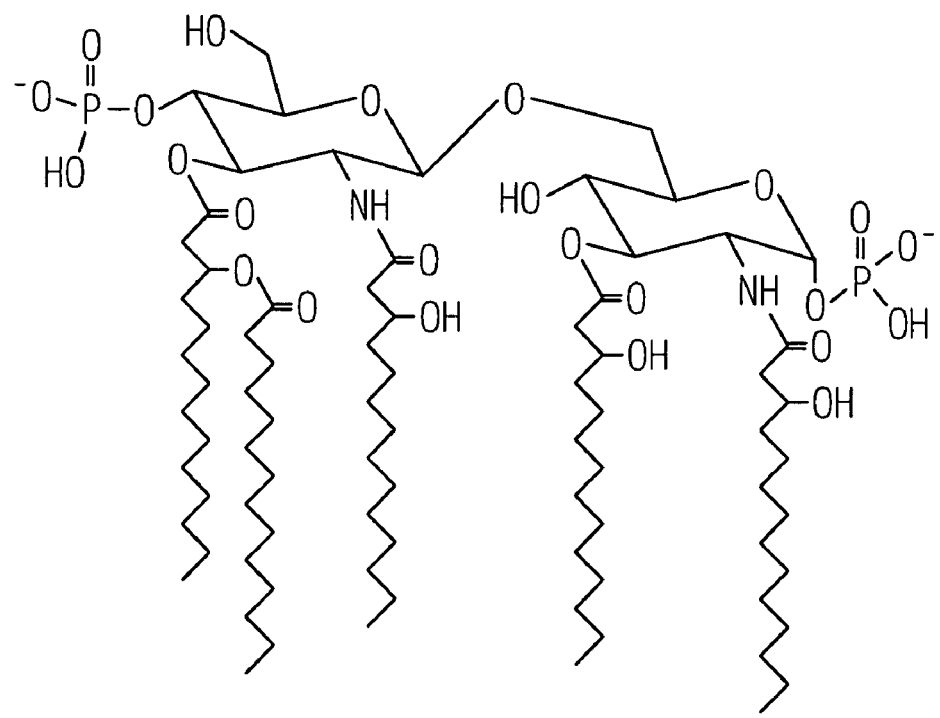
Figure 2A:
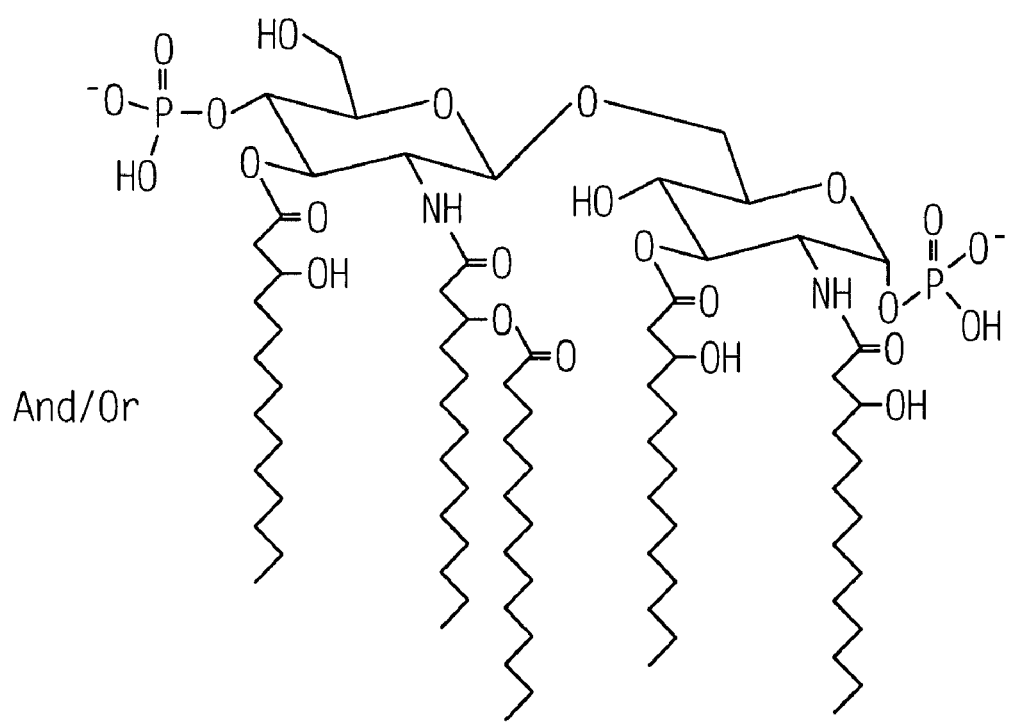
Figure 2B:
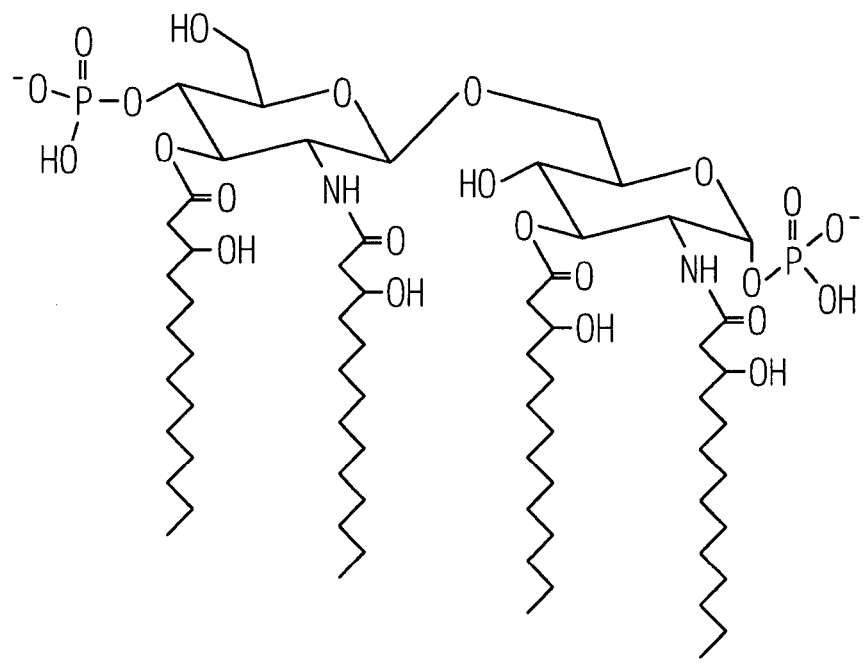

The discoveries comprising the present invention include the unexpected results that knockout mutations of the htrB gene of gram-negative bacteria (including the family Enterobacteriaceae) result in htrB mutants which specifically lack one or more secondary acyl chain fatty acids which are ester-bound to the hydroxyl groups of two of the four molecules of β-OH (as shown in FIG. 2). Thus, it appears that the htrB protein has either acyltransferase activity, or indirectly or directly affects regulation of acyltransferase activity. The following examples are presented to illustrate preferred embodiments of aspects of the present invention, and are not intended to limit the scope of the invention. In particular, a preferred embodiment is the making of an *H. influenzae* htrB mutant, and methods of using the same as a whole cell, or to isolate therefrom the endotoxin, in vaccine preparations or to generate antibodies for therapeutic or diagnostic applications. However, since the lipid A moiety is highly conserved among bacteria of the family Enterobacteriaceae and closely related gram-negative bacteria, the invention relates to gram-negative bacterial pathogens, as defined previously herein. There is microheterogeneity in terms of the length of the secondary acyl chain (12 or 14 carbon chains) and to which of the four β-OH are substituted (1, 2, or 4) (Erwin et al., 1991, *Infect Immun* 59:1881–1887); however, the nature of the substitution is the same and thus the particular steps (genes and gene products) involved in the biosynthetic pathway appear conserved. For example, removal of secondary acyl chains from various gram-negative bacterial pathogens (*E. coli, H. influenzae, P. aeruginosa, S. typhimurium*, and *N. meningitidis*) using human acyloxyacy hydrolase resulted in deacylated LPS from all species tested having significantly reduced mitogenic activity (Erwin et al., 1991, supra) as compared to the respective wild type strain.

EXAMPLE 1

Identification of an htrB Gene, and Generation of htrB Mutants

By complementing a nontypable *H. influenzae* strain 2019 with a *S. typhimurium* rfaE mutant strain, the rfaE gene of *H. influenzae* strain 2019 was cloned (Lee et al., 1995, *Infect Immun* 63:818–824). Sequence analysis of the upstream region of the *H. influenzae* rfaE gene revealed an open reading frame highly homologous to the *E. coli* htrB gene. The *H. influenzae* htrB gene comprises 933 bases and encodes a protein, HtrB, of 311 amino acids (SEQ ID NO:1) and an estimated molecular size of 36 kilodaltons (kDa). Comparison of the deduced amino acid sequence of the *H. influenzae* HtrB with the *E. coli* HtrB revealed shared homology (56% identity and 73% similarity). Cloning the htrB gene of *H. influenzae* into a plasmid, and subsequent in vitro transcription-translation analysis, revealed that HtrB has an apparent molecular size of 32–33 kDa.

There are various standard techniques known to those skilled in the art for mutating a bacterial gene. Those techniques include site-directed mutagenesis, and shuttle mutagenesis using transposons. In one aspect of this embodiment, mutagenesis of the htrB gene was carried out by shuttle mutagenesis. A derivative of the bacterial transposon Tn3, mini-Tn3 (Seifert et al., 1986, *Proc. Natl. Acad. Sci. USA* 83:735–739), was used as an insertion sequence to mutate the htrB gene. A 2.4 kilobase (kb) BglII containing the htrB gene from *H. influenzae* was cloned into a plasmid which was used as a target for mini-Tn3 transposon mutagenesis. Briefly, introduced into a single bacterial cell (*E. coli*), is the plasmid containing the htrB gene; a plasmid immune to Tn3 transposition and containing transposase (which mediates the cointegration between Tn3 and the target molecules); and a plasmid containing mini-Tn3.

After allowing for transposition, the bacterial cells are mated with an *E. coli* strain containing the cre enzyme that is used to resolve cointegrates in shuttle mutagenesis. Transconjugates were selected for with antibiotics (kanamycin, ampicillin, and streptomycin) and analyzed by restriction endonuclease digestion.

Two plasmids, termed pB28 and pB29, each with a mini-Tn3 transposon containing the chloramphenicol acetyltransferase (CAT) gene inserted into the htrB open reading frame at a different location. Nontypeable *Haemophilus influenza* strains 2019 B28 and 2019 B29 were deposited on Nov. 14, 2000 with the American Type Culture Collection, 10801 University Blvd., Manassas, Va. 20110–2209 under the provisions of the Budapest Treaty, and all restrictions will be irrevocably removed upon the granting of a patent on this application. Strain B28 has been accorded accession number PTA-2667 and strain B29 has been accorded accession number PTA-2668. Each plasmid was used to transform nontypeable *H. influenzae* strain 2019 and bacterial cell transformants were selected for by growth in the presence of chloramphenicol (1.5 µg/ml), resulting in identification of mutant strains designated NTHi B28 and B29, respectively. Locations of the mTn3 insertion in the chromosomes of the NTHi mutants were confirmed by genomic Southern hybridization using the 2.4 kb BglII fragment as a probe. In particular, a BglII digest of NTHi strain 2019 DNA resulted in a 2.4 kb fragment; whereas similar digests of DNA from mutants NTHi B28 and B29 revealed 4.0 kb fragments. Further, the 4.0 kb fragments were digested by EcoRI which is present in the mTn3.

Alternatively, methods are known in the art to perform site-directed mutagenesis into a bacterial gene (See for example, Halladay, 1993, *J. Bacteriol.* 175:684–692), and recombination of the mutated bacterial gene into the bacterial chromosome. A selectable kanamycin resistance cassette may be used to insert into, and mutate, the htrB gene contained within a shuttle plasmid. Subsequent transformation into a bacterial host cell with the shuttle plasmid, and recombination of the bacterial genome (at the site of the genomic copy of the htrB gene) with the cassette via htrB flanking sequences, results in the site-directed mutagenesis of the bacterial htrB gene.

Primer extension analysis can be used to determine the promoter region of the htrB gene. The *H. influenzae* htrB's promoter region was determined by primer extension analysis by first growing the bacteria, harvesting and purifying the RNA, and using a commercial primer extension kit according to the manufacturer's suggestions. A single transcription site was found using a primer (SEQ ID NO:2) complementary to the 5' region of the htrB open reading frame. The first nucleotide was a cytosine (C) residue located at 21 bp upstream of the putative translation start site, ATG. The region upstream of the transcription start site contained a sequence (SEQ ID NO:1, bases 13 to 29) similar to the consensus −10 region of the bacterial $\sigma^7$-dependent promoters at an appropriate distance. An element (SEQ ID NO:1, bases 1 to 6) resembles the consensus sequence of the −35 region.

EXAMPLE 2

Characterization of htrB Mutants

Growth Characteristics

NTHi B28 and B29 strains were initially selected at 30° C., and were unable to grow at 37° C. With further passages at 30° C., the NTHi htrB mutants began to lose temperature sensitivity and demonstrated a slow rate of growth, as compared to NTHi 2019, at 37° C. However, for growth temperatures greater than or equal to 38.5° C., the temperature sensitivity remained for the htrB mutants.

It was reported previously that *E. coli* htrB mutants demonstrated a change in membrane permeability to various compounds including kanamycin and deoxycholate (Karow et al., 1992, supra). The NTHi htrB mutants were also tested for sensitivity to kanamycin and deoxycholate. Overnight cultures grown at 30° C. were then diluted and allowed to grow in the presence of 5 µg/ml kanamycin at either 30° C. or 37° C. At 30° C., no difference was detected in the growth rate between NTHi 2019 and the NTHi htrB mutant strains in the absence of kanamycin. However, the growth of the htrB mutants was significantly inhibited in the presence of kanamycin, whereas NTHi 2019 was not affected. For the htrB mutants, the sensitivity to kanamycin was even greater at 37° C., since the mutants failed to show growth in the presence of kanamycin at 37° C. Likewise, at 30° C. the htrB mutants showed sensitivity, as compared to NTHi strain 2019, at concentrations of greater than 500 µg/ml deoxycholate, and failed to grow at 1000 µg/ml. At 37° C., the htrB mutants showed almost complete inhibition of growth in the presence of only 250 µg/ml deoxycholate.

Endotoxin Characteristics

The LPS of *E. coli* htrB mutants has been characterized as being weakly stained on silver-stained polyacrylamide gels, but its migration pattern did not vary as compared to LPS from wild type. In contrast, the LOS from NTHi mutants B28 and B29 migrated faster than that from NTHi strain 2019 on silver-stained gels. Additionally, the LOS from the B28 and B29 mutants displayed a brownish color rather than black, as displayed by NTHi 2019. Reconstitution, by introducing a plasmid with an intact htrB gene into the mutant, of NTHi mutant B29 confirmed that the differences in growth characteristics and LOS migration and staining were due to mutation of the htrB gene.

The NTHi htrB mutant LOS and wild type LOS were each analyzed by electrospray ionization-mass spectrometry (ESI-MS) to provide molecular mass profiles for the different components of LOS. First, LOS was isolated from the respective strains. LPS or LOS can be isolated by the phenol-water method (Westphal et al., 1965, *Methods in Carbohydrate Chemistry* 5:83–91); or using an alternative purification procedure (using a protease; Hitchcock et al., 1983, *J. Bacteriol.* 154:269–277). The isolated LOS species were then O-deacylated by mild hydrazine treatment (37° C. for 20 minutes; see Phillips et al., 1990, *Biomed. Environ. Mass Spectrom.* 19:731–745). Analysis by ESI-MS of the different LOS species showed that while the O-deacylated LOS from NtHi mutant B29 and NTHi 2019 were similar in molecular mass profile, two differences can be clearly discerned. In the htrB mutant, there is a decrease (50% reduction) in the amount of LOS containing two phosphoethanolamines (PEA) in the inner core structure; and there is a shift to high molecular weight LOS species containing more hexoses. These findings suggest that the degree of phosphorylation may be affecting chain progression from specific heptose moieties, and that HtrB either directly or indirectly affects phosphorylation of LOS.

Mass spectrometry was used to analyze the lipid A. More specifically, lipid A from htrB mutant LOS and from wild type LOS were each analyzed by liquid secondary ion mass spectrometry (LSIMS) in the negative ion mode to provide a spectrum of molecular ions for the different components lipid A. First, the LOS species were each hydrolyzed in 1% acetic acid for 2 hours at 100° C. at a concentration of 2 mg/ml. The hydrolysates were centrifuged, and the supernatants removed. The water soluble crude lipid A fractions were washed twice in water, and once in an organic mixture (chloroform/methanol/water; by volume 2:1:1) and then evaporated to dryness. For analysis, the lipid samples were redissolved in $CH_2Cl_2/CH_3OH$ (3:1, v/v) and 1 μl of nitrobenzylalcohol/triethanolamine (1:1, v/v) and applied as a liquid matrix onto a mass spectrometer.

LSIMS of the wild type (NTHi 2019) revealed a spectrum containing two deprotonated molecular ions consistent with a hexaacyl lipid A structure containing either one (hexaacyl monophosphoryl lipid A, $M_r$=1744) or two phosphates (hexaacyl diphosphoryl lipid A, $M_r$=1824).

This spectrum is essentially identical to that reported for the lipid A structure of LOS of *H. ducreyi* (Melaugh et al., 1992, *J. Biol. Chem.* 267:13434–13439). The lower mass fragments are believed to be ions which arise through LSIMS-induced fragmentation of higher ass mono- and diphosphorylated molecular ion species.

In contrast, the LSIMS spectrum for the lipid A preparation from the htrB mutant LOS lacks molecular ions corresponding to the wild type hexaacyl lipid A species. There are two high mass ions which correspond to the molecular ions for a mono- and diphosphoryl pentaacyl lipid A species missing one of the secondary acyl chains (e.g. myrisitic acid moiety). Further, at the lower masses are two additional molecular ion species that correspond to a mono- and diphosphoryl tetraacyl lipid A species lacking both secondary acyl chains. In summary, the lipid A structure of the wild type's LOS is hexaacyl; whereas the lipid A structure of the htrB mutant shows two species, a tetraacyl (FIG. 2A) and a pentaacyl species (FIG. 2B) indicating the loss of at least one, and sometimes both secondary acyl chains. The htrB mutant is comprised of approximately 90% tetraacyl lipid A with only the four hydroxymyristic acid ester and amide-linked fatty acids, and approximately 10% pentaacyl lipid A with one myristic acid substitution.

EXAMPLE 3

Substantially Reduced Toxicity of HtrB Mutants

The effect due to the lack of one or more secondary acyl chains on the toxicity of a gram-negative bacterial pathogen was examined using a standard in vitro assay for measuring in vivo toxicity. Murine macrophage-like cell line J774, when stimulated by endotoxin, secretes TNFα. The amount of TNFα, a directly proportional to the toxicity of the stimulating LPS or LOS, can be measured by (a) removing the cell-free supernatant containing the TNFα; (b) adding the supernatant to a TNFα-sensitive cell line, such as WEHI 164; and (c) measuring the resultant cytotoxicity (See for example, Espevik et al., 1986, *J Immunol Methods* 95:99; Sakurai et al., 1985, *Cancer Immunol Immunother* 20:6–10; Adams et al., 1990, *J Clin Microbiol* 28:998–1001; Adams et al., 1990, *J Leukoc Biol* 48:549–56; Tsai et al., 1992, *Cell Immunol* 144:203–16; and Pfister et al., 1992, *Immunol* 77:473–6).

In this assay, adherent J774 cells were removed from culture, washed with PBS-1 mM EDTA, and then washed twice with complete tissue culture medium without antibiotics. $2 \times 10^6$ to $4 \times 10^6$ J774 cells/100 mm culture dish were incubated in tissue culture medium overnight in a $CO_2$ incubator. Adherent J774 cells are removed with PBS-1 mM EDTA, washed three times in tissue culture medium, and adjusted to $5 \times 10^5$/ml. Aliquots of 50 μl were added per well of a round bottom 96 well plate. The plate is then incubated for 1 hour at 37° C. in a $CO_2$ incubator. Per well is added either an htrB mutant, or the wild type strain, in various colony forming units (cfu, infection dose). The plate is then incubated at 37° C. for 1 hour in a $CO_2$ incubator. After the incubation, 100 μl of culture medium containing 50 μg/ml gentamycin is added per well. The plate is then incubated overnight at 37° C. in a $CO_2$ incubator. Aliquots of 50l of the J774 supernatant were removed per well and transferred into wells of a flat bottom 96 well plate. Serial 10 fold dilutions were made of the J774 supernatant. Included as a control is a dilution series of recombinant TNFα (rTNFα). Added per well is 50l of WEHI 164 clone 13 cells at $6 \times 10^5$ cells/ml in tissue culture medium +25 mM LiCl +2 μg/ml actinomycin D; and the mixture was incubated overnight at 37° C. in a $CO_2$ incubator. After the incubation, 10l of alomar blue is added, and 5–7 hours later the optical density is read at 570 nm. The assay utilizes alomar blue as a color indicator; i.e., alomar blue is converted to a red color by living cells, but remains blue if the cells are killed.

Figure 3:
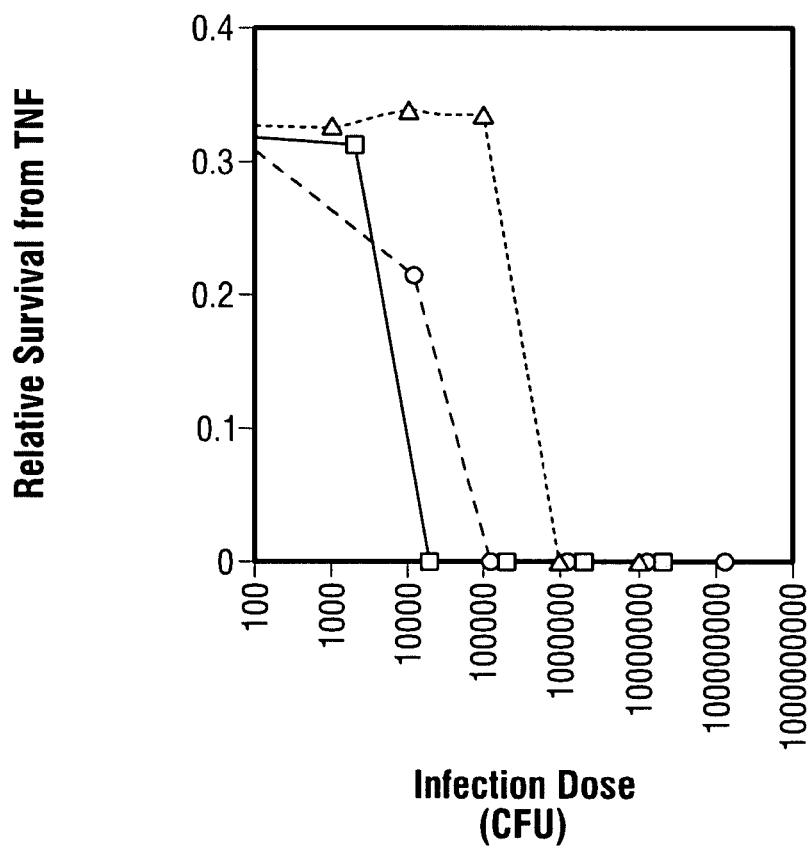

FIG. 3 shows a comparison between the number of bacterial cells of *H. influenzae* strain 2019 (wild type, □), and of bacterial cells of htrB mutant NTHi B29 (○ and △) necessary to stimulate the release of enough TNFα from J774 cells to kill the TNFα-susceptible cell line WEHI 164. $B29_{hi}$ (△) and $B29_{LO}$ (○) refer to a high number (>3) and low number (<3) of passages of htrB mutant, respectively. As shown in FIG. 3, the htrB mutant shows a reduced ability to stimulate TNFα release; i.e., between an approximately 10 fold reduction ($B29_{LO}$) to an approximately 100 fold reduction (B29$_{hi}$). This reduced ability to stimulate TNFα is one indication of the htrB mutant being substantially reduced in toxicity due to the lack of one or more secondary acyl chains in the lipid A portion of the endotoxin.

Figure 4:
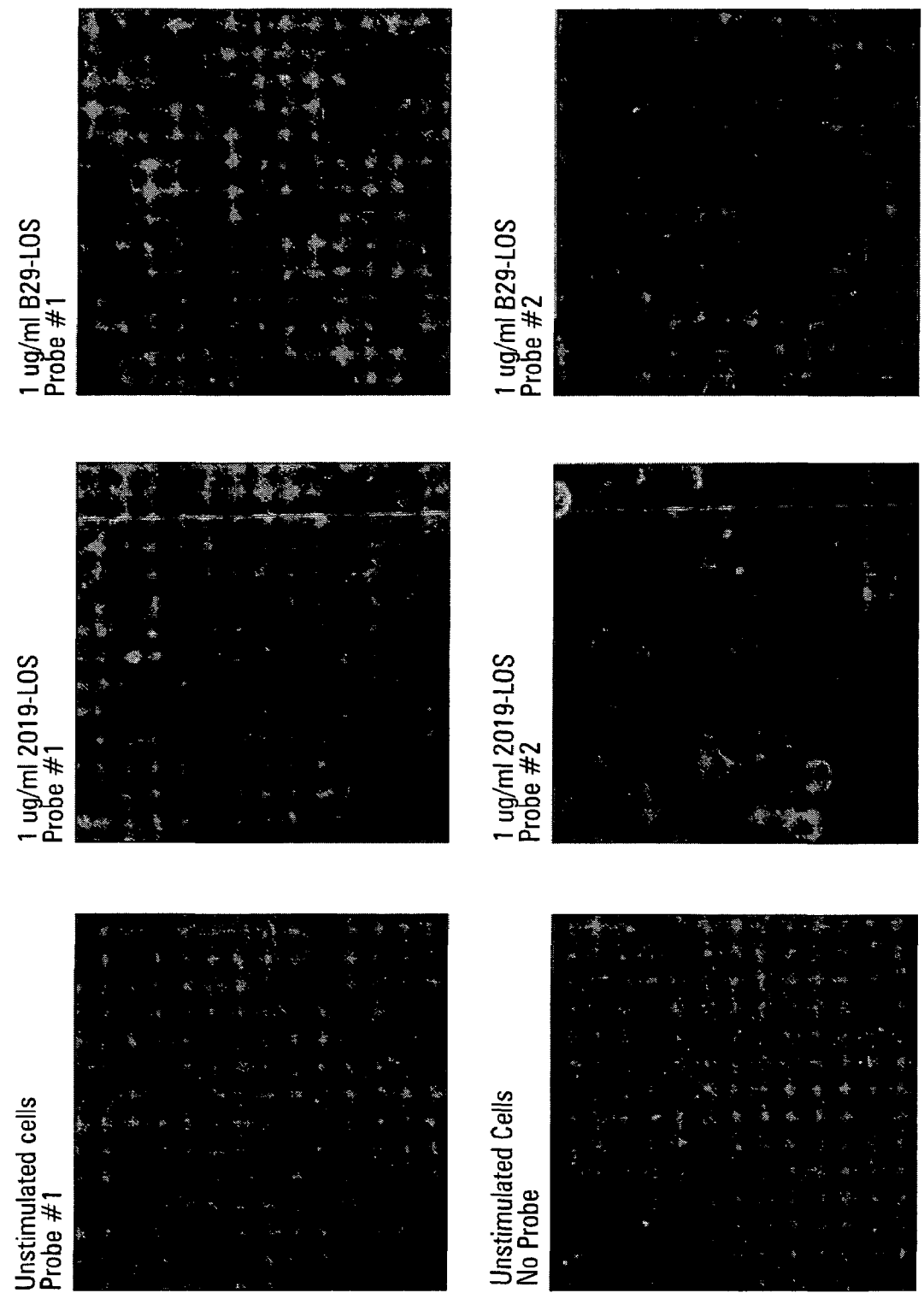

The effect due to the lack of one or more secondary acyl chains on the toxicity of a gram-negative bacterial pathogen was also examined using a standard in situ assay for measuring in vivo toxicity. SV-40 transformed human respiratory epithelial cells and human primary respiratory epithelial cells, when stimulated by endotoxin, produces TNFα which production can be demonstrated by detection of TNFα mRNA using methods known to those skilled in the art for in situ hybridization (a modification of MacNaul et al., 1990, J. Immunol. 145:4154–66). The cells are grown in a monolayer within wells of a 24-well plate until approximately confluent. To stimulate the cells, 1 μg/ml of LOS is added, and the cells are incubated overnight at 37° C. A counterstain (e.g., membrane stain) is added and the cells are then fixed with 0.5 ml of 2% paraformaldehyde in buffer so that the counterstain is fixed directly into the cells. Hybridization is then performed using an oligonucleotide probe specific for TNFα RNA (SEQ ID NO:4), and a control probe (SEQ ID NO:5). The amount of TNFα mRNA visually detected is directly proportional to the toxicity of the stimulating LPS. TNF mRNA was minimally induced in SV-40 transformed human respiratory epithelial cells, and human primary respiratory epithelial cells (FIG. 4), exposed to LOS isolated from the htrB mutant NTHi B29. This is in contrast to LOS isolated from parent strain NTHi 2019 which induced high levels of TNFα mRNA in these human respiratory cells (FIG. 4) and cell lines.

The substantial reduction in toxicity exhibited by the htrB mutant, as observed by the TNFα assays, due to the lack of one or more secondary acyl chains is further supported by previously reported assays of bioactivity of endotoxin treated with acyloxyacyl hydrolase which selectively removes the secondary acyl chains from endotoxin. Deacylated endotoxin from E. coli, H. influenzae, N. meningitidis, and S. typhimurium were (a) similarly reduced in potency in the Limulus lysate test relative to the respective wild type endotoxin; (b) reduced in the ability to stimulate neutrophil adherence to human endothelial cells relative to the respective wild type endotoxin; and (c) reduced in mitogenic activity for murine splenocytes (Erwin et al., 1991, Infect Immun 59:1881–1887); yet maintained expression of antigenic epitopes. Similarly, S. typhimurium LPS treated with acyloxacyl hydrolase showed a reduction in toxicity by 100-fold or greater in a dermal Shwartzman reaction; was less pyrogenic in a thermal response model; showed a 5 to 12 fold reduction in B-cell mitogenicity; and showed a 10 to 20 fold reduction in the release of prostaglandin E$_2$, as compared to wild type endotoxin, in concluding that maximally deacylated LPS was at least 10 fold less toxic than wild type endotoxin (U.S. Pat. No. 4,929,604).

EXAMPLE 4

Use of htrB Mutants as Immunogens

In one aspect of this embodiment, the htrB mutant of a gram-negative bacterial pathogen is used as a whole cell vaccine. The benefit of using live, attenuated (weakened in its ability to cause pathogenesis) bacteria as an immunogen in a vaccine formula is that they are able to survive and may persist in the human or animal body, and thus confer prolonged immunity against disease. In conjunction with the benefit of using a live bacteria to prolong the immune response, gram-negative bacterial pathogen htrB mutants have the added benefit in that they exhibit substantially reduced toxicity. Another advantage, as compared to a vaccine formulation comprising an isolated peptide representing a bacterial antigen, is that a bacterial antigen expressed on the surface of a bacterial cell will often result in greater stimulation of the immune response. This is because the surface of bacteria of the family Enterobacteriaceae acts as a natural adjuvant to enhance the immune response to an antigen presented thereon (Wezler, 1994, Ann NY Acad Sci 730:367–370). Thus, using a live bacterial vaccine, such as an htrB mutant, to express complete proteins in a native conformation (i.e., as part of the bacterial outer membrane) is likely to elicit more of a protective immune response than an isolated protein alone.

Live bacterial vaccine vectors of the family Enterobacteriaceae that have been described previously include attenuated Salmonella strains (Stocker et al., U.S. Pat. Nos. 5,210,035; 4,837,151; and 4,735,801; and Curtiss et al., 1988, Vaccine 6:155–160; herein incorporated by reference), and Shigella flexneri (Sizemore et al., 1995, Science 270: 299–302; herein incorporated by reference). One preferred embodiment is to provide a vaccine delivery system for human or animal (depending on the genus and species of the gram-negative bacterial pathogen) mucosal pathogens. Thus, immunization by the parental route or by the mucosal route with a prophylactically effective amount of the htrB mutant, or an htrB mutant transformed to recombinantly express additional bacterial antigens (that do not negatively affect the growth or replication of the transformed htrB mutant), can lead to colonization of mucosal surfaces to induce mucosal immunity against the antigens displayed on the surface of, or secreted from the htrB mutant. The resultant htrB mutant can be used in a vaccine formulation which expresses the bacterial antigen(s).

Similar methods can be used to construct an inactivated htrB mutant vaccine formulation except that the htrB mutant is inactivated, such as by chemical means known in the art, prior to use as an immunogen and without substantially affecting the immunogenicity of the expressed immunogen(s). For example, human bronchial mucosal immunity has been stimulated with an aerosol vaccine comprising lysed H. influenzae (Latil et al., 1986, J Clin Microbiol 23:1015–1021). Either of the live htrB mutant vaccine or the inactivated htrB mutant vaccine may also be formulated with a suitable adjuvant in order to further enhance the immunological response to the antigen(s) expressed by the vaccine vector, as to be described in more detail.

In another aspect of this embodiment, the endotoxin is isolated from the htrB mutant using methods known in the art, and the isolated htrB endotoxin is used in a vaccine formulation. As mentioned previously, major antigenic determinants of gram-negative bacteria are believed to reside in the carbohydrate structure of the O-specific side chain of LPS and the complex carbohydrate structure of LOS. However, the chemical nature of LPS and LOS prevent the use of these molecules in vaccine formulations; i.e., active immunization with LPS or LOS is unacceptable due to the inherent toxicity of the secondary acyl chains of the lipid A portion of endotoxin. The endotoxin isolated from an htrB mutant of a gram-negative bacterial pathogen lacks one or more secondary acyl chains, and thus exhibits substantially reduced toxicity as compared to endotoxin isolated from the respective wild type bacteria. Therefore, endotoxin isolated from an htrB mutant of a gram-negative bacterial pathogen can be used in a vaccine formulation in inducing immunity against the respective wild type gram-negative bacterial pathogen. LPS or LOS can be isolated by the phenol-water method (Westphal et al., 1965, *Methods in Carbohydrate Chemistry* 5:83–91); or using an alternative purification procedure (using a protease; Hitchcock et al., 1983, *J. Bacteriol.* 154:269–277).

Many methods are known for the introduction of a vaccine formulation into the human or animal (collectively referred to as "individual") to be vaccinated. These include, but are not limited to, intradermal, intramuscular, intraperitoneal, intravenous, subcutaneous, ocular, intranasal, and oral administration. Conventionally, vaccine formulations containing either live bacteria, or attenuated or inactivated bacteria, are administered by injection or by oral administration. For example, respiratory immunity can be stimulated by intestinal immunization with purified *H. influenzae* antigens (Cripps et al., 1992, *J. Infect Dis* 165S1:S199–201; herein incorporated by reference). The vaccine formulation may comprise a physiologically acceptable solution as a carrier in which the htrB mutant bacterial cells or isolated htrB mutant endotoxin is suspended. Various adjuvants may be used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc. The vaccine formulation is administered in a prophylactically effective amount to be immunogenic, which depends on factors including the individual's ability to mount an immune response, the degree of protection to be induced, and the route of administration.

In another aspect of the invention, the vaccine formulation can be administered orally by including it as part of the feed given to economically important livestock. As known by those skilled in the art, species of *Haemophilus, Campylobacter, Pseudomonas,* and *Salmonella* are pathogenic for economically important livestock. Using the methods according to the present invention, as illustrated in the following examples, htrB mutants of such animal pathogens can be produced. The resultant htrB mutants, or endotoxin isolated therefrom, can be used in a vaccine formulation. Use of vaccine formulations, containing one or more antigens of various microbial pathogens, in animal feed has been described previously (See for example, Pritchard et al., 1978, *Avian Dis* 22:562–575).

EXAMPLE 5

*H. influenzae* htrB Mutants as Immunogens

In one embodiment, the htrB mutant is an *H. influenzae* htrB mutant. *Haemophilus influenzae* is an important human respiratory tract pathogen in diseases including otitis media, chronic sinusitis, and chronic obstructive pulmonary disease. Certain surface-exposed bacterial components, including P2, P6, and LOS, appear to be antigens which may confer a protective immune response in immunized humans. Such antigens have been shown to be targets of bactericidal antibody, and the presence of serum bactericidal antibody is associated with protection from infection by *H. influenzae* (Faden et al., 1989, *J. Infect. Dis.* 160:999–1004).

5.1 In one aspect of the this embodiment, the endotoxin isolated from an htrB mutant is used as the immunogen in a vaccine formulation. As demonstrated in Example 3 herein, the endotoxin isolated from an htrB mutant of a gram-negative bacterial pathogen lacks one or more secondary acyl chains, and thus exhibits substantially reduced toxicity as compared to endotoxin isolated from the respective wild type bacterial pathogen. Therefore, endotoxin isolated from an htrB mutant of *H. influenzae* can be used in a vaccine formulation in inducing immunity against the respective wild type strain. The htrB mutant LOS may be isolated by a method known to those skilled in the art for isolating LOS. The htrB mutant LOS may be used in a vaccine formulation containing one or more agents selected from the group consisting of a pharmaceutically acceptable carrier (e.g., a physiological solution), an adjuvant, or a carrier protein.

Figure 5:
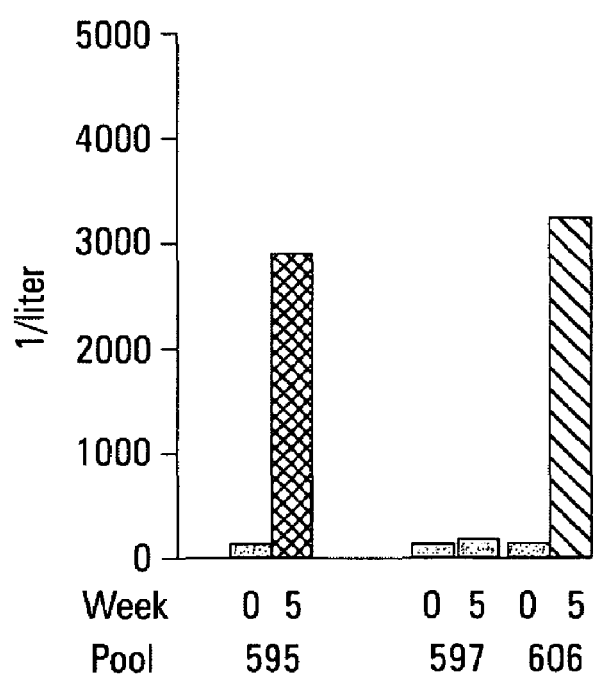
Figure 6:
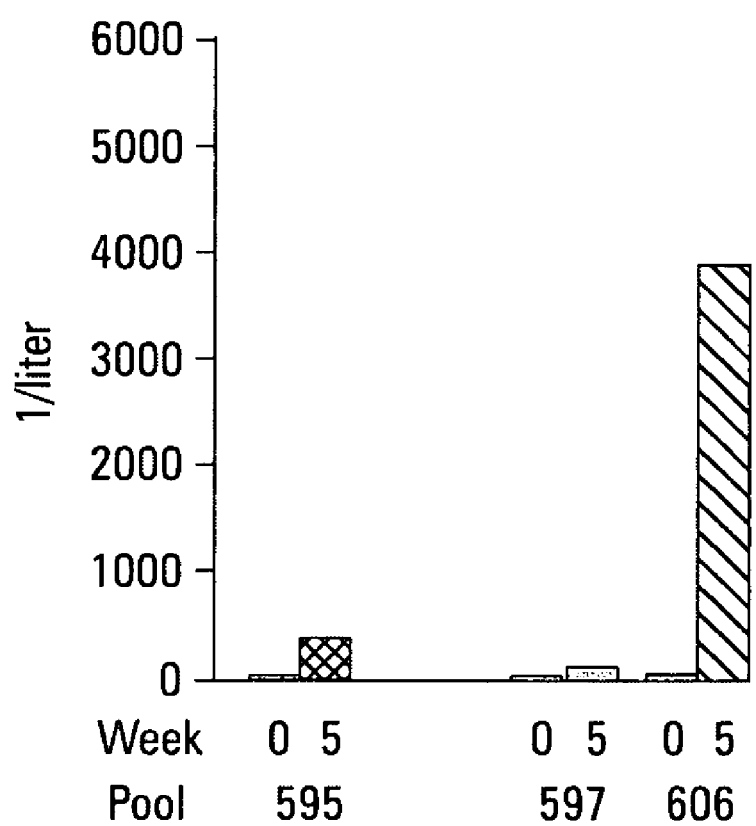

To illustrate the effects of immunization with htrB mutant LOS, a mouse model was used. NTHi 2019 LOS, and htrB mutant NTHi B29 LOS were each isolated from their respective strains using the phenol-water method. Groups of at least 5 Swiss Webster mice-were-immunized subcutaneously with 1 µg of either NTHi 2019, htrB mutant B29 LOS, or htrB mutant conjugated to a carrier protein, with adjuvant QS-21. Sera was Collected from each group 5 weeks after immunization, and the sera from animals comprising a group were pooled. The pooled sera was assessed for titer of anti-LOS antibody by enzyme-linked immunosorbent assay (ELISA). Microtiter wells of ELISA plates were coated with either 10 µg of NTHi 2019, or htrB mutant B29 LOS. FIG. 5 illustrates the mean titers of anti-LOS antibody against NTHI 2019 LOS (antigen coating) in ELISA from mice immunized with NTHi 2019 (Pool 595), htrB mutant B29 LOS (Pool 597), or htrB mutant B29 LOS conjugated to a carrier protein (Pool 606). FIG. 6 illustrates the mean titers of anti-LOS antibody against htrB mutant B29 LOS (antigen coating) in ELISA from mice immunized with NTHi 2019 (Pool 595), htrB mutant B29 LOS (Pool 597), or htrB mutant B29 LOS conjugated to a carrier protein (Pool 606). Preimmune sera was also included as a control ("week 0" or "time 0").

The antibody induced by the different LOS preparations were then tested for functional activity by performing bactericidal assays using NTHi 2019 as the target. Into the wells of a 96-well plate are added 0.150 ml buffer, 0.040 ml pooled human sera as a complement source, and 0.0 ml of NTHi 2019. Typically, the organism is plated in a dilution (e.g. 20 to 200 cfu). Into test wells are added the respective antisera either undiluted ("neat"), 1/10 dilution, or 1/100 dilution. The plate is then rotated vigorously (175–2001 rpm) at 37° C. for 30 minutes. Aliquots from respective wells are plated on media and grown to determine percentage survival, and log kill. Log kill is calculated as the log(cfu 30 minutes/cfu time 0). The results of the bactericidal assay are shown in Table 1, where Group R595 is the antisera induced by NTHI 2019 LOS, Group R597 is the antisera induced by htrB mutant B29 LOS, and Group R606 is the antisera induced by htrB mutant B29 LOS conjugated to a carrier protein.

TABLE 1

| Group | week | dilution | % survival | log kill |
|---|---|---|---|---|
| R595 | 0 | neat | 1.00 | −1.99 |
| | | 1/10 | 37.30 | −0.43 |
| | | 1/100 | 87.20 | −0.06 |
| | 5 | neat | — | −4.49 |
| | | 1/10 | 0.07 | −3.15 |

TABLE 1-continued

| Group | week | dilution | % survival | log kill |
|---|---|---|---|---|
|  |  | 1/100 | 20.20 | −0.70 |
|  | 7 | 1/10 | — | −4.62 |
|  |  | 1/100 | 7.80 | −1.11 |
| R597 | 0 | neat | 3.50 | −1.46 |
|  |  | 1/10 | 62.40 | −0.20 |
|  |  | 1/100 | 108.60 | 0.04 |
|  | 5 | neat | — | −4.49 |
|  |  | 1/10 | 4.40 | −1.36 |
|  |  | 1/100 | 82.40 | −0.08 |
|  | 7 | 1/10 | — | −4.49 |
|  |  | 1/100 | 99.80 | 0.00 |
| R606 | 0 | neat | 0.13/110.5 | −2.87/0.92 |
|  |  | 1/10 | 130.20 | 0.11 |
|  |  | 1/100 | 106.50 | 0.03 |
|  | 5 | neat | 1.5/0.1 | −1.81/−2.9 |
|  |  | 1/10 | 25.10 | −0.60 |
|  |  | 1/100 | 164.10 | 0.22 |
|  | 7 | 1/10 | 0.04 | −3.44 |
|  |  | 1/100 | 185.90 | 0.27 |

The greater the log kill (the more negative the number, e.g. −4.49), the greater the bactericidal activity is of the respective antibody. Thus, for comparison purposes, at week 7 and at a 1/10 dilution, log kill for the antisera induced by NTHi 2019 LOS is −4.62, the log kill for the antisera induced by NTHi htrB mutant B29 LOS is −4.49, and the log kill of the antisera induced by htrB mutant B29 LOS conjugated to a carrier protein is −3.44. By ELISA, it looks like the antisera induced by htrB mutant B29 LOS antibody is low in titer; yet, as demonstrated by the bactericidal assays, significant functional antibody is raised by immunization with htrB mutant B29 LOS.

5.2 In another aspect of the this embodiment, htrB mutant bacterial cells are used as the immunogen in a vaccine formulation. To illustrate the effects of immunization with htrB mutant bacterial cells, an infant rat model was used. The use of the infant rat model as a model of bacteremic infections due to type b *H. influenzae* (Hib) in humans, and for determining the virulence of type b *H. influenzae* strains, has been accepted by those skilled in the art (see, e.g., Smith et al., 1973, *Infect. Immun.* 8:278–290; Moxon et al., 1974, *J. Infect. Dis.* 129:154–62; Rubin et al., 1983, *Infect. Immun.* 41:280–284; Zwahlen et al., 1985, *J. Infect. Dis.* 152:485–492).

Type b strain A2 of *H. influenzae* has already been characterized as a highly virulent strain in the infant rat model system that causes bacteremia and meningitis after inoculation (e.g., intraperitoneal or intranasal), and as a clinical isolate from humans (it isolated from a child with meningitis due to *H. influenzae*). Using the methods according to Example 1, an htrB mutant was made from Hib strain A2. One week old infant Sprague-Dawley albino rats were inoculated intraperitoneally with either 1 Hib strain A2 or $10^7$ htrB A2 mutant and then assessed for intravascular clearance by measuring the number of colony forming units (cfus) per ml of blood obtained 48 hours post-inoculation. The results showed that 20 of 20 infant rats inoculated with Hib strain A2 showed bacteremia, with all rats showing greater than $10^5$ cfu/ml of strain A2. In contrast, only 13 of 20 infant rats inoculated with htrB A2 mutant showed bacteremia, with only 10 of the 13 showing greater than $10^5$ cfu/ml of htrB A2 mutant.

Similarly, one week old infant Sprague-Dawley albino rats were inoculated intranasally with either $10^7$ Hib strain A2 or $10^7$ htrB A2 mutant and then assessed for intravascular clearance. The results showed that 8 of 20 infant rats inoculated with Hib strain A2 showed bacteremia, with 7 of those 8 rats showing greater than 105 cfu/ml of strain A2. In contrast, none of the 30 infant rats inoculated with htrB A2 mutant showed bacteremia. Taken together, it can be concluded from this model system that htrB mutants demonstrate attenuated virulence, as compared to its wild-type strain, as indicated by the decreased ability to cause bacteremia (e.g., a 30% reduction in the occurrence of bacteremia).

To further illustrate the effects of immunization with htrB mutant bacterial cells, a chinchilla model was used. The use of the chinchilla model as a model of middle ear infections due to nontypable *H. influenzae* (NTHi) in humans, and for determining the virulence of NTHi strains, has been accepted by those skilled in the art (see, e.g., Bakaletz et al., 1989, *Acta Otolaryngol.* 107:235–243; Madore et al., 1990, *Pediatrics* 86:527–34; Barenkamp, 1986, *Infect. Immun.* 52:572–78; Green et al., 1994, *Methods Enzymol.* 235:59–68).

NTHi 2019 is a clinical isolate described previously (see, e.g., Murphy et al., 1986, *Infect. Immun.* 54:774–779). Each healthly adult chinchilla was inoculated, via the epitympanic bulla into the middle ear space, with various log doses of either NTHi 2019 or htrB mutant NTHi B29. The course of middle ear disease was then assessed by periodic otoscopic examination for tympanic membrane inflammation or middle ear infusion, and aspiration from the middle ear with subsequent culture. The results showed that when compared to NTHi 2019, it takes up to a 3 log greater dose of htrB mutant NTHi B29 ($10^7$ cfu/ear) to induce middle ear infection. It can be concluded from this model system that htrB mutants demonstrate attenuated virulence, as compared to its wild-type strain, as indicated by the decreased ability to cause middle ear disease.

In another aspect of this embodiment the *H. influenzae* htrB mutant is genetically engineered to express one or more heterologous bacterial antigens. As will be discussed in more detail below, *H. influenzae* has a natural genetic transformation process involving linearized DNA binding, uptake via one or more uptake sequences (e.g. AAGTGCGGT—SEQ ID NO:3), translocation, and recombination. Thus, one mechanism to introduce a recombinant DNA molecule containing the at least one heterologous bacterial antigen to be expressed, is to transform the host *H. influenzae* htrB mutant with linearized recombinant DNA molecule containing the DNA encoding the at least one heterologous bacterial antigen ("the encoding sequence"). Alternatively, the recombinant DNA molecule containing the encoding sequence to be expressed can be inserted into a plasmid vector, and either introduced into as a linearized recombinant molecule by the natural transformation process; as circularized recombinant plasmid using electroporation of noncompetent *H. influenzae* htrB mutants; or as a circularized recombinant plasmid transformed into competent *H. influenzae* htrB mutants.

Plasmids useful for cloning of and expression from recombinant DNA molecules in *H. influenzae* are known to those skilled in the art. Such plasmids include:

pRSF0885 confers ampicillin resistance, and contains a PvuII cloning site and a defective TnA sequence (Setlow et al., 1981, *J. Bacteriol.* 148:804–811), and can replicate in both *H. influenzae* and *E. coli* (Trieu et al., 1990, *Gene* 86:99–102).

pDM2 was constructed by cloning chloramphenicol resistance into pRSF0885; and pDM5 was constructed by cloning tetracycline resistance into pRSF0885 (McCarthy et al., 1986, *J. Bacteriol.* 168:186–191).

pVT63, pVT64, pVT65, pVT66 are improved shuttle vectors for *H. influenzae* and *E. coli* based on pDM2 (Trieu et al., 1990, *Gene* 86:99–102), and contain the pUC-derivative of the ColE1 ori, and the pRSF0885 rep locus. Additionally, each plasmid has drug markers with unique restriction sites for insertional inactivation of the drug marker as follows: pVT63-ApR (HincII, PstI, ScaI), KmR (ClaI, HindIII, NruI, SmaI, XhoI); pVT64-ApR (HincII, PstI, ScaI, SspI), SpR; pVT65-ApR (HincII, PstI, ScaI, PvuI, SspI), CmR (BalI, NcoI); pVT66-ApR (HincII, PstI, ScaI, PvuI), CmR (SmaI).

pACYC177, pACYC184, pSU2718, pSU2719 are improved shuttle vectors for *H. influenzae* and *E. coli* based on p15A (Chandler, 1991, *Plasmid* 25:221–224), have the p15A ori, and were compatible with a plasmid containing the RSF0885 origin of replication. Additionally, each plasmid has multiple cloning sites restriction sites and drug markers as follows: pACYC177-ApR, KmR (Accession No. X06402); pACYC184-CmR, TcR (Accession No. X06403); pSU2718-CmR and polycloning site from pUC18 (Accession No. M64731); and pSU2719-CmR and polycloning site from pUC19 (Accession No. M64732).

pQL1 is an improved shuttle vector for use in *H. influenzae* and *E. coli* containing both the pMB1 ori and P15a ori, KmR which is flanked by *H. influenzae* uptake sequences, a multiple cloning site containing a unique BamHI and SmaI restriction sites, and which is particularly suited for analyzing *H. influenzae* promoter strength in *H. influenzae* (Heidecker et al., 1994, *Gene* 150:141–144).

In cloning the recombinant DNA molecule containing the encoding sequence into a plasmid vector, one skilled in the art will appreciate that the choice of restriction enzymes for digesting both the recombinant DNA molecule and the plasmid to result in compatible ends for ligation depends on the unique restriction enzyme sites at the ends of the recombinant DNA molecule, whether occurring naturally or engineered such as during enzymatic amplification; one or more unique restriction enzyme sites within the plasmid vector; whether insertion into the plasmid vector will assist in the selection process (See, e.g., pVT66); and whether a plasmid-derived promoter is used solely, or in addition to the promoter(s) of the encoding sequences, to drive expression from the recombinant DNA molecule. Selection and screening of transformed *H. influenzae* htrB mutants may be accomplished by methods known in the art including detecting the expression of a marker gene (e.g., drug resistance marker) present in the plasmid, and immunodetection of the expressed and displayed heterologous bacterial antigen. While this aspect of the embodiment illustrates that the recombinant DNA molecule containing the encoding sequence can be inserted into a plasmid and expressed in *H. influenzae* htrB mutants, it will be appreciated by those skilled in the art that vectors other than plasmids, can be used including, but not limited to, bacteriophage vectors.

Successful expression of the at least one heterologous bacterial antigen requires that either the recombinant DNA molecule comprising the encoding sequence, or the vector itself, contain the necessary control elements for transcription and translation which is compatible with, and recognized by the particular host system used for expression. Using methods known in the art of molecular biology, including methods described above, various promoters and enhancers can be incorporated into the vector or the recombinant DNA molecule containing the encoding sequence to increase the expression of the heterologous bacterial antigen, provided that the increased expression of the heterologous bacterial antigen(s) is compatible with (for example, non-toxic to) the htrB mutant. As referred to herein, the encoding sequence can contain DNA encoding more than one heterologous bacterial antigen, and may include viral and/or fungal antigen-encoding sequences, to create a multivalent antigen for use as an improved vaccine composition.

The selection of the promoter will depend on the expression system used. For example, a preferred promoter in an *H. influenzae* expression system may be the P2 or P6 promoter operatively linked to the encoding sequence. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted encoding sequence.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the encoding sequence to increase transcriptional efficiency. These or other regulatory sites, such as transcription or translation initiation signals, can be used to regulate the expression of the encoding sequence. Such regulatory elements may be inserted into the recombinant DNA molecule containing the encoding sequence, or nearby vector DNA sequences using recombinant DNA methods described herein, and known to those skilled in the art, for insertion of DNA sequences.

Accordingly, a recombinant DNA molecule containing an encoding sequence, can be ligated into an expression vector at a specific site in relation to the vector's promoter, control, and regulatory elements so that when the recombinant vector is introduced into the htrB mutant, the heterologous bacterial antigen can be expressed in the host cell. The recombinant vector is then introduced into the htrB mutant, and the transformed htrB mutants are selected, and screened for those cells containing the recombinant vector. Selection and screening may be accomplished by methods known in the art, and depending on the vector and expression system used.

The introduction of a recombinant DNA molecule containing the encoding sequence (including an expression vector or plasmid containing the same) into *H. influenzae* htrB mutants can be accomplished in any one of three processes: a natural genetic transformation process; transformation of competent bacterial cells; and electroporation of non-competent bacterial cells.

Natural Transformation Process

The natural genetic transformation process of *H. influenzae* involves linearized DNA binding, uptake via one or more uptake sequences, translocation, and recombination. Thus, one mechanism to introduce a recombinant DNA molecule containing the encoding sequence to be expressed into at least one heterologous bacterial antigen, is to transform the host *H. influenzae* with linearized recombinant DNA molecule containing the encoding sequence; or a linearized vector having inserted into it the recombinant DNA molecule containing the encoding sequence to be expressed. In this natural process, when the linearized DNA is translocated intracellularly, one of the translocated strands of DNA is apparently degraded by exonuclease activity (Barany et al., 1983, *Proc. Natl. Acad. Sci. USA* 80:7274–7278). If the translocated strand lacks homology sufficient for recombination into the *H. influenzae* chromosome, the translocated strand becomes susceptible to further degradation (Pifer et al., 1985, *Proc. Natl. Acad. Sci. USA* 82:3731–3735). Using methods known in the art (e.g., Barany et al., 1983, supra; herein incorporated by reference), linearized DNA containing the encoding sequence can be introduced into *H. influenzae* htrB mutants. Since the encoding sequence can be flanked by *H. influenzae* sequences, to increase the likelihood of recombination of the encoding sequence into the *H. influenzae* htrB mutants' genome is likely to occur.

Transformation of Competent Bacterial Cells

Another mechanism to introduce a recombinant DNA molecule containing the encoding sequence to be expressed into at least one heterologous bacterial antigen, is to transform competent host *H. influenzae* htrB mutants with a circular vector, such as a plasmid, having inserted into it the recombinant DNA molecule containing the encoding sequence to be expressed. Competence of *H. influenzae* develops best under conditions in which the bacterial cell duplication is inhibited, such as a temporary shift to anaerobic conditions, by physiological change occurring during late-log phase growth, and transfer of cells into nutrient-poor, chemically-defined medium. Such defined media for the development of competence of *H. influenzae* has been previously described in detail (Herriott et al., 1970*, J. Bacteriol.* 101:517–524; herein incorporated by reference). It appears that only a short time after entering competent H. influenzae, a plasmid containing sequences homologous to the bacterial chromosome can insert its homologous sequence (such as the encoding sequence flanked by *H. influenzae* sequences) into the chromosome via recombination (Setlow et al., 1981, supra). for expression. Thus, in this embodiment, a plasmid containing the encoding sequence which is capable of being transformed into competent *H. influenzae* htrB mutants is introduced by methods for transformation known in the art (Karudapuram et al., 1995*, J. Bacteriol.* 177:3235–3240; Setlow et al., 1981, supra, herein incorporated by reference). The encoding sequence may then be recombined into the *H. influenzae* htrB mutants' genome where it is expressed under the control of its own promoter or an *H. influenzae* promoter near the site of insertion. Such transformation is reported to be at a relatively high frequency (McCarthy and Cox, 1986*, J. Bacteriol.,* 168:186–191).

Alternatively, transformation of competent *H. influenzae* htrB mutants by a circular plasmid with the appropriate origin(s) of replication and containing the encoding sequence may result in plasmid establishment; i.e., a plasmid coexisting as an extrachromosomal element without recombination. Examples of such plasmids have been described above. Thus, in this variation of the embodiment, a plasmid containing the encoding sequence which is capable of being transformed into, and established in, competent *H. influenzae* htrB mutants is introduced by methods for transformation known in the art. The encoding sequence is then expressed from the plasmid under the control of its own promoter or a promoter within the vector.

Electroporation of Non-Competent Bacterial Cells

Yet another mechanism to introduce a recombinant DNA molecule containing the encoding sequence to be expressed into at least one heterologous bacterial antigens, is to introduce a circular vector, such as a plasmid having inserted into it the recombinant DNA molecule containing the encoding sequence to be expressed, into non-competent host *H. influenzae* htrB mutants by electroporation. Electroporation has been used to efficiently introduce plasmid DNA into bacteria. However, optimal conditions may differ depending on the host cell used. Optimal conditions have been described for electroporating plasmid DNA into *H. influenzae* (Mitchell et al., 1991*, Nucl. Acids Res.* 19:3625–3628; herein incorporated by reference). It was found that electroporation of plasmid into *H. influenzae* made competent by defined, nutrient poor media was several orders of magnitude less efficient than electroporation into non-competent *H. influenzae*. Thus, in this variation of the embodiment, it would be preferred that a plasmid containing the encoding sequence is electroporated into non-competent *H. influenzae* htrB mutants. The plasmid is capable of being established in *H. influenzae* htrB mutants, or is degraded after the encoding sequence has recombined into the *H. influenzae* htrB mutants' genome. In either case, the encoding sequence is under the control of its own promoter; or a promoter within the vector or genome, respectively.

EXAMPLE 6

Neisserial htrB Mutants as Immunogens

In another embodiment, the htrB mutant is a Neisserial htrB mutant selected from the group including *Neisseria gonorrhoeae*, and *Neisseria meningitidis*. *N. gonorrhoeae* is a gram-negative bacterial pathogen causing the sexually transmitted disease gonorrhea, which subsequently can lead to pelvic inflammatory disease in females. *N. meningitidis* is a gram-negative bacterial pathogen which can cause a variety of clinical infections including bacteremia, septicemia, meningitis, and pneumonia. Alterations in the terminal glycosylation of the LOS of *Neisseria* are believed correlate with serum sensitivity and serum resistance of the organism. Further, protective bactericidal antibody is directed against type-specific antigens of *N. meningitidis*, wherein the type-specific antigens have been identified as outer membrane proteins, or LOS, or both.

Using the methods according to the present invention, as illustrated in Examples 1–3 and 10, htrB mutants of a Neisserial species can be produced and identified. One skilled in the art, using the htrB gene of *H. influenzae*, can isolate the htrB gene of the Neisserial species, and produce a mutated htrB gene (unable to encode functional HtrB) using transposon mutagenesis with subsequent recombination resulting in a Neisserial htrB mutant lacking one or more secondary acyl chains. Alternatively, there may be sufficient homology between *Neisseria* and *Haemophilus* to use plasmids pB28 and pB29, each with a mini-Tn3 transposon containing the chloramphenicol acetyltransferase (CAT) gene inserted into the htrB open reading frame at a different location, to transform the Neisserial species for recombination of the mutant htrB gene into the Neisserial htrB gene. Neisserial transformants are then selected for by growth in the presence of chloramphenicol (1.5 μg/ml), resulting in identification of Neisserial htrB mutant strains. Locations of the mTn3 insertion in the chromosomes of the Neisserial htrB mutants may be confirmed by genomic Southern hybridization using a probe containing htrB sequences. The resultant Neisserial htrB mutants can then be tested for substantially reduced toxicity using assays described by those skilled in the art for measuring the toxic effects induced by endotoxin.

Using the methods according to the present invention, as illustrated in Examples 4 & 5, endotoxin isolated from a Neisserial htrB mutant can be used in a vaccine formulation in inducing immunity against the wild type strains of Neisserial pathogens. The htrB mutant LOS may be isolated by a method known to those skilled in the art for isolating LOS. The htrB mutant LOS may be used in a vaccine formulation containing one or more agents selected from the group consisting of a pharmaceutically acceptable carrier (e.g., a physiological solution), an adjuvant, or a carrier protein.

Alternatively, Neisserial htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into Neisserial species are known to those skilled in the art, including: pLES2 confers ampicillin resistance, is a shuttle vector functional in both *E. coli* and *N. gonorrhoeae*, and contains a polylinker with restriction sites for EcoRI, SmaI, and BamHI (Stein et al., 1983, *Gene* 25:241–247). Neisserial species also contain a natural transformation process (Rudel et al., 1995, *Proc Natl Acad Sci USA* 92:7896–90; Goodman et al., 1991, *J Bacteriol* 173: 5921–5923); and can also be made competent or be electroporated using techniques known to those skilled in the art.

EXAMPLE 7

*Haemophilus* Ducreyi htrB Mutants as Immunogens

In another embodiment, the mutant is a *H. ducreyi* htrB mutant. *H. ducreyi* is a gram-negative bacterial pathogen causing a genital ulcer disease, chancroid. Using the methods according to the present invention, as illustrated in Examples 1–3 and 10, *H. ducreyi* htrB mutants can be produced and identified. One skilled in the art, using the htrB gene of *H. influenzae*, can isolate the htrB gene of *H. ducreyi*, and produce a mutated htrB gene (unable to encode functional HtrB) using transposon mutagenesis with subsequent recombination resulting in an *H. ducreyi* htrB mutant lacking one or more secondary acyl chains. Alternatively, there is likely sufficient homology between *H. ducreyi* and *H. influenzae* to use plasmids pB28 and pB29, each with a mini-Tn3 transposon containing the chloramphenicol acetyltransferase (CAT) gene inserted into the htrB open reading frame at a different location, to transform *H. ducreyi* for recombination of the mutant htrB gene into the *H. ducreyi* htrB gene. *H. ducreyi* transformants are then selected for by growth in the presence of chloramphenicol (1.5 µg/ml), resulting in identification of *H. ducreyi* htrB mutant strains. Locations of the mTn3 insertion in the chromosomes of the *H. ducreyi* htrB mutants may be confirmed by genomic Southern hybridization using a probe containing htrB sequences. The resultant *H. ducreyi* htrB mutants can then be tested for substantially reduced toxicity using assays described by those skilled in the art for measuring the toxic effects induced by endotoxin.

Using the methods according to the present invention as illustrated in Examples 4 & 5, endotoxin isolated from an *H. ducreyi* htrB mutant can be used in a vaccine formulation in inducing immunity against the wild type strains of *H. ducreyi*. The htrB mutant LOS may be isolated by a method known to those skilled in the art for isolating LOS. The htrB mutant LOS may be used in a vaccine formulation containing one or more agents selected from the group consisting of a pharmaceutically acceptable carrier (e.g., a physiological solution), an adjuvant, or a carrier protein.

Alternatively, *H. ducreyi* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Haemophilus* species are known to those skilled in the art, as disclosed in Example 5; and can also be made competent or be electroporated using techniques known to those skilled in the art, as disclosed in Example 5.

EXAMPLE 8

*Campylobacter jejuni* htrB Mutants as Immunogens

In another embodiment, the mutant is a *C. jejuni* htrB mutant. *Campylobacter jejuni* is a gram-negative bacterial pathogen causing human enteritis. Infection by *C. jejuni* has also been associated with the onset of neurologic disorders such as Guillian-Barré syndrome. *C. jejuni* htrB mutants can be produced and identified using the methods according to the present invention, as illustrated in Examples 1–3 and 10. One skilled in the art, using the htrB gene of *H. influenzae*, can isolate the htrB gene of *C. jejuni*, and produce a mutated htrB gene (unable to encode functional HtrB) using transposon mutagenesis with subsequent recombination resulting in an *C. jejuni* htrB mutant lacking one or more secondary acyl chains.

Alternatively, there may be sufficient homology between *C. jejuni* and *H. influenzae* to use plasmids pB28 and pB29, each with a mini-Tn3 transposon containing the chloramphenicol acetyltransferase (CAT) gene inserted into the htrB open reading frame at a different location, to transform *C. jejuni* for recombination of the mutant htrB gene into the *C. jejuni* htrB gene. *C. jejuni* transformants are then selected for by growth in the presence of chloramphenicol (1.5 µg/ml), resulting in identification of *C. jejuni* htrB mutant strains. Locations of the mTn3 insertion in the chromosomes of the *C. jejuni* htrB mutants may be confirmed by genomic Southern hybridization using a probe containing htrB sequences. The resultant *C. jejuni* htrB mutants can then be tested for substantially reduced toxicity using assays described by those skilled in the art for measuring the toxic effects induced by endotoxin.

Using the methods according to the present invention, as illustrated in Examples 4 & endotoxin isolated from a *C. jejuni* htrB mutant can be used in a vaccine formulation in inducing immunity against the wild type strains of *C. jejuni*. The htrB mutant LPS may be isolated by a method known to those skilled in the art for isolating LPS. The htrB mutant LPS may be used in a vaccine formulation containing one or more agents selected from the group consisting of a pharmaceutically acceptable carrier (e.g., a physiological solution), an adjuvant, or a carrier protein.

Alternatively, *C. jejuni* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *C. jejuni* are known to those skilled in the art, and includes: pUA466 confers tetracycline resistance, and contains an unique AvaI site and AvaII site (Taylor, 1986, *J Bacteriol* 165:1037–39). *C. jejuni* can also be made competent or be electroporated using techniques known to those skilled in the art.

EXAMPLE 9

*Moraxella catarrhalis* htrB Mutants as Immunogens

In another embodiment, the mutant is a *M. catarrhalis* htrB mutant. *Moraxella catarrhalis* is a gram-negative bacterial pathogen causing otitis media in children; sinusitis and conjunctivitis in children and adults; and lower respiratory tract infections, septicemia, and meningitis in immunocompromised hosts. *M. catarrhalis* htrB mutants can be produced and identified using the methods according to the present invention, as illustrated in Examples 1–3 and 10. One skilled in the art, using the htrB gene of *H. influenzae*, can isolate the htrB gene of *M. catarrhalis*, and produce a mutated htrB gene (unable to encode functional HtrB) using transposon mutagenesis with subsequent recombination resulting in an *M. catarrhalis* htrB mutant lacking one or more secondary acyl chains. Alternatively, there may be sufficient homology between *M. catarrhalis* and *H. influenzae* to use plasmids pB28 and pB29, each with a mini-Tn3 transposon containing the chloramphenicol acetyltransferase (CAT) gene inserted into the htrB open reading frame at a different location, to transform *M. catarrhalis* for recombination of the mutant htrB gene into the *M. catarrhalis* htrB gene. *M. catarrhalis* transformants are then selected for by growth in the presence of chloramphenicol (1.5 µg/ml), resulting in identification of *M. catarrhalis* htrB mutant strains. Locations of the mTn3 insertion in the chromosomes of the *M. catarrhalis* htrB mutants may be confirmed by genomic Southern hybridization using a probe containing htrB sequences. The resultant *M. catarrhalis* htrB mutants can then be tested for substantially reduced toxicity using assays described by those skilled in the art for measuring the toxic effects induced by endotoxin.

Using the methods according to the present invention, as illustrated in Examples 4 & 5, endotoxin isolated from a *M. catarrhalis* htrB mutant can be used in a vaccine formulation in inducing immunity against the wild type strains of *M. catarrhalis*. The htrB mutant LOS may be isolated by a method known to those skilled in the art for isolating LPS. The htrB mutant LOS may be used in a vaccine formulation containing one or more agents selected from the group consisting of a pharmaceutically acceptable carrier (e.g., a physiological solution), an adjuvant, or a carrier protein.

Alternatively, *M. catarrhalis* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *M. catarrhalis* are known to those skilled in the art. *M. catarrhalis* contains a natural transformation process (Juni, 1977, *J Clin Microbiol* 5:227–35) and can also be made competent or be electroporated using techniques known to those skilled in the art.

EXAMPLE 10

*Salmonella* htrB Mutants as Immunogens

In another embodiment, the mutant is a *Salmonella* htrB mutant. *Salmonella* species comprise gram-negative bacteria that can cause a variety of clinical illnesses in humans and animals. For example, *S. typhi* is the causative agent of typhoid fever in humans. *S. paratyphi* is a causative organism of a fever known as *salmonella* fever in humans. Salmonellosis, a gastroenteritis in humans, can be caused by various species in the genus *Salmonella* (typhimurium, newport, heidelberg, and enteritidis). *Salmonella* htrB mutants can be produced and identified. One skilled in the art, using the htrB gene of a gram-negative bacterial pathogen, can produce a mutated htrB gene (unable to encode functional HtrB) using transposon mutagenesis and subsequent recombination, ultimately resulting in an *Salmonella* htrB mutant having a modification in one or more secondary acyl chains. The resultant *Salmonella* htrB mutants can then be tested for substantially reduced toxicity using assays described by those skilled in the art for measuring the toxic effects induced by endotoxin.

To illustrate this embodiment, and using methods similar to those in Example 1 herein, mutagenesis of the htrB gene was carried out by shuttle mutagenesis by mini-Tn10 (conferring tetracycline resistance) used as an insertion sequence to mutate the htrB gene. The htrB:Tn10 was then transfered from *E. coli* to a virulent *S. typhimurium* by transduction. Using methods previously described (Masters, 1996, in *E. coli* and *Salmonella* Cellular and Molecular Biology, vol. 2, 2nd edition, p. 2421, ASM Press), a r⁻m⁺ galE mutS recD *S. typhimurium* (SL5283) was sequentially transduced with MST3488 (recD542:Tn10d which confers chloramphenicol resistance (cm$^r$)) via *Salmonella* phage P22 resulting in a r⁻m⁺galE muts recD cm$^r$ *S. typhimurium* ("MGS-1"), and then with MST3063 (mutS:Tn10 which confers tertracycline resistant (tet$^r$)) resulting in a r⁻m⁺ galE muts recD cm$^r$ tet$_r$ *S. typhimurium* ("MGS-3") *S. typhimurium* MGS-3 was cured of TN10 by selection for tetracycline sensitivity on media using methods previously described (Bochner et al., 1990, *J. Bacterial.* 143:926–933) resulting in a r⁻m⁺ galE muts recD cm$^r$ *S. typhimurium* ("MGS-7"). For confirmation purposes, it was shown that *S. typhimurium* MGS-7 showed the same response to ultraviolet light as the parental strain MGS-3.

An *E. coli* strain ("MLK217") containing the htrB:mini TN10 was used to transfer the htrB:Tn10 by transduction into *S. typhimurium* MGS-7 via coliphage P1 according to methods previously described (Masters, 1996, supra), and selected for by growth at 30° C. on media plates containing tetracycline. The result of the transduction, and after reisolation for tetracycline-resistant clones, was the creation of a r⁻ m⁺ galE muts recD htrB:mini Tn10 cm$^r$ tet$^r$ *S. typhimurium* ("MGS-23"). *S. typhimurium* MGS-23 was tested for one or more of the phenotypic properties associated with htrB mutation, namely (1) temperature sensitivity; (2) filamentation and bulging at non-permissive temperatures; and (3) deoxycholate resistance. The results of the phenotypic analysis indicated that MGS-23 carried the miniTn 10 element inserted within the *S. typhimurium* htrB gene because MGS-23 was able to grow at 30° C. but not at 37° C.; formed many filamentous forms when shifted to non-permissive temperature; and showed resistance to higher concentrations of deoxycholate (7.5% to 10%) than the isogenic parent (2.5%). The mutation of the htrB was further confirmed by analysis using polymerase chain reaction.

A virulent *S. typhimurium* strain (SL1344) was transduced to htrB:Tn10 from *S. typhimurium* MGS-23 via *Salmonella* phage P22 and selection at 30° C. on media plates containing tetracycline. After isolation, resultant tetracycline resistant clones having the same phenotype as MGS-23 were further analyzed. One such clone, MGS-31, was shown to have a mutated htrB gene, by complementing the clone using a plasmid with a wild type htrB gene (Karow et al., 1991, *J. Bacteriol.* 173:741–50; Karow et al., 1991, *Mol. Microbiol.*

5:2285–2292) thereby returning the clone to the wild type phenotype of normal growth, normal cell morphology, deoxycholate sensitivity at 37° C., and wild type virulence.

Endotoxin Characteristics

Figure 7:
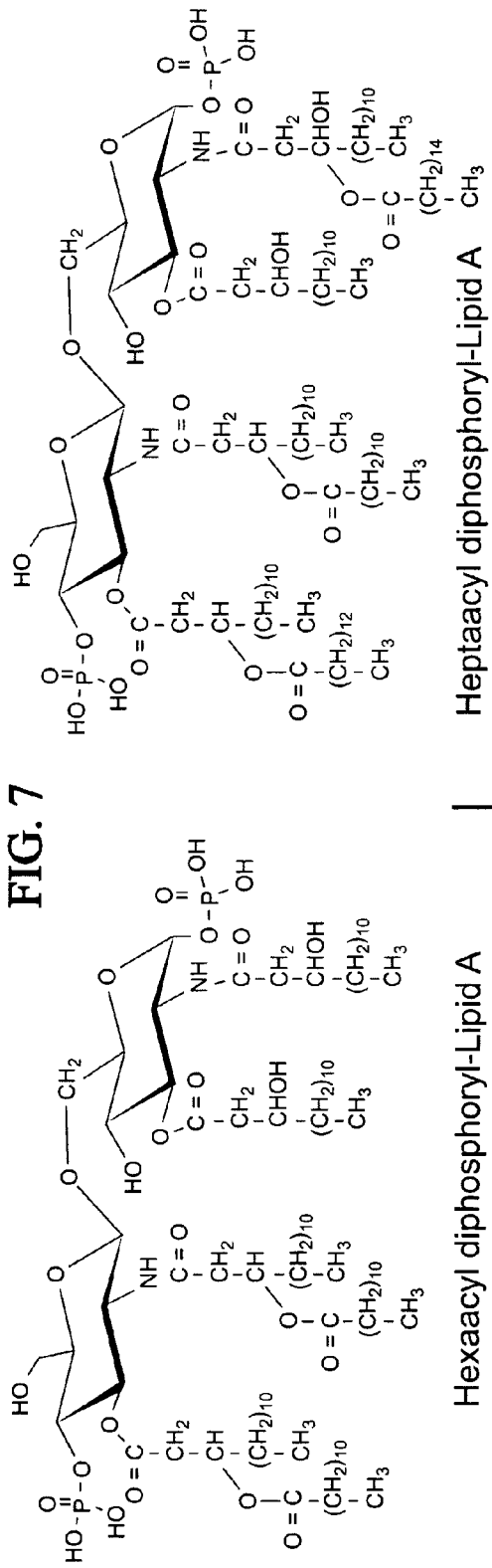
Figure 7:
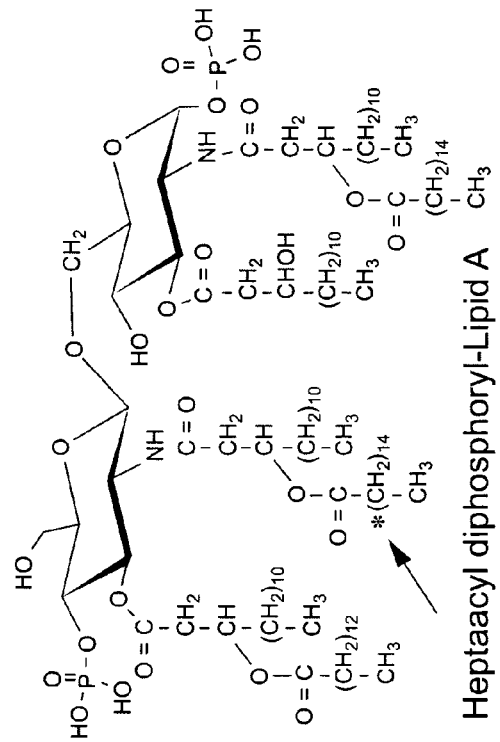
Figure 7:
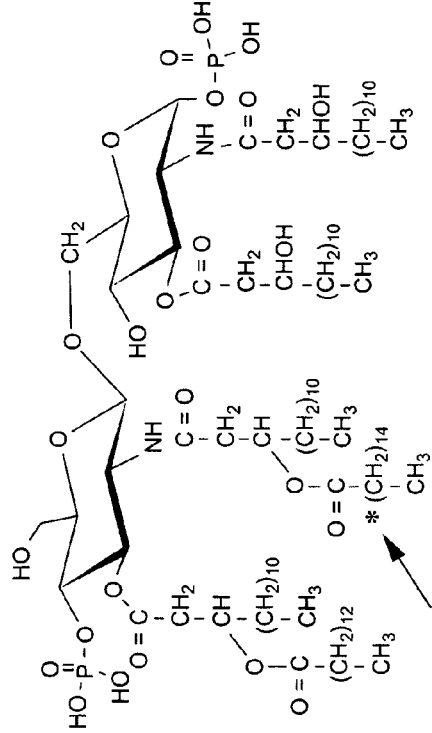

Mass spectrometry was used to analyze the lipid A according to the methods in Example 2 herein. More specifically, lipid A from *S. typhimurium* htrB mutant LPS and from wild type *S. typhimurium* LPS were each analyzed by liquid secondary ion mass spectrometry (LSIMS) in the negative ion mode to provide a spectrum of molecular ions for the different components lipid A. The chemical analysis of the lipid A of the *S. typhimurium* htrB mutant indicated that the modifications in the lipid A structure that occurred were similar, but not identical, to modifications in the lipid A structure seen in *H. influenzae* htrB mutants. In the wild type *S. typhimurium* lipid A contains either six (hexaacyl) or seven (heptaacyl) fatty acid substitutions from the diglucosamine backbone (FIG. 7). In the wild type strain, on glucosamine II, the 3' substitution on the N-linked C14 fatty acid (hexaacyl or heptaacyl) is a C12 fatty acid. In contrast, and as shown in FIG. 7, the C12 fatty acid is replaced with a C16 fatty acid. These results indicate that the *S. typhimurium* htrB gene encodes an acyltransferase responsible for placing the C12 fatty acid at the 3' position on the N-linked C14 fatty acid. Mutation of the *S. typhimurium* htrB gene results in the functional induction of another acyltransferase which places a C16 fatty acid at the 3' position on the N-linked C14 fatty acid. It is known to those skilled in the art, that lipid A is crucial for the survival of a gram-negative organism, and for the proper organization of its outer membrane. Thus, and as related to virulence and toxicity of the organism, the effects of the htrB gene mutation in *S. typhimurium* was analyzed.

Endotoxin Toxicity

A mouse model system that is used by those skilled in the art as relevant to human disease, is the D-galactosamine model. In the D-galactosamine model, the sensitivity to LPS is increased by exposure to D-galactosamine (Galanos et al., 1986, *Infect. Immun.* 51:891–896) thereby achieving the same lethality and TNF induction with low doses of LPS, i.e. with levels of endotoxin commensurate with those identified in the blood of septic patients. Thus, D-galactosamine-treated mice exposed to LPS is a standard animal model system accepted by those skilled in the art as relevant to endotoxic shock in humans. In this model, groups of 4 mice were treated with D-galactosamine (8 mg) simultaneously with the administration of the dosage of the LPS to be tested. Groups of 4 mice each were injected with either 0.001 µg, 0.01 µg, 0.1 µg, 1 µg or 10⁻ µg of the purified LPS to be tested and the number of mice surviving the challenge at each dose were checked every 24 hours for 5 days after the injection. The $LD_{50}$ (lethal dose where 50% of the mice are killed) is then calculated. The purified LPS to be separately tested included LPS from the wild type virulent *S. typhimurium* strain 1344; and the *S. typhimurium* htrB mutant (MGS-31). The results show that the $LD_{50}$ for mice injected with LPS from *S. typhimurium* strain 1344 is 0.01 µg. In contrast, the $LD_{50}$ for mice injected with LPS from *S. typhimurium* htrB mutant MGS-31 is 0.1 µg. Thus, the lipid A from the *S. typhimurium* htrB mutant is at least 10 fold less toxic than the lipid A of the wild type strain.

Virulence

Since mice are naturally susceptible to infection by *S. typhimurium*, like humans, a second mouse model was used to assess the effects of the htrB mutation on virulence of *S. typhimurium*. Typically, from approximately 50 cfu to 100 cfu will kill 50 to 100% of the mice injected. The strains used included *S. typhimurium* strain 1344; *S. typhimurium* htrB mutant (MGS-31); and the *S. typhimurium* htrB mutant which was complemented by the plasmid containing an intact htrB gene (MGS-43). The respective organisms were injected intraperitoneally in a dosage ranging from $5 \times 10^1$ to $5 \times 10^7$ cfu and watched over 5 days. Generaly, 100% of the animals who will die from bacteremia, do so within that period. As may be expected, the $LD_{50}$ for the virulent *S. typhimurium* strain 1344 was less than $5 \times 10^1$ cfu. Likewise, the $LD_{50}$ for the *S. typhimurium* htrB mutant which was complemented with the intact htrB gene, MGS-43, also was less than $5 \times 10^1$ cfu. In contrast, the $LD_{50}$ for the *S. typhimurium* htrB mutant MGS-31 was $9.7 \times 10^6$ cfu, an approximately $2 \times 10^5$ reduction in virulence compared to the wild type virulent strain. *S. typhimurium* htrB mutant growth in vivo in mice was confirmed by culturing and assaying liver and spleen for bacterial counts. The results suggest that the htrB mutation in *Salmonella* has a more profound effect on virulence factors than just a modification of the LPS.

Using the methods according to the present invention, as illustrated in Examples 4 & 5, endotoxin isolated from a *Salmonella* htrB mutant can be used in a vaccine formulation in inducing immunity against the wild type strains of the *Salmonella* species. The htrB mutant LPS may be isolated by a method known to those skilled in the art for isolating LPS. The htrB mutant LPS may be used in a vaccine formulation containing one or more agents selected from the group consisting of a pharmaceutically acceptable carrier (e.g., a physiological solution), an adjuvant, or a carrier protein.

Alternatively, *Salmonella* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Salmonella* are known to those skilled in the art, and includes:

pYA260 containing lacZ cloned into a trc promoter; and pJW270 conferring tetracycline resistance and containing lacI (Ervin et al., 1993 *Microb Pathogen* 15:93–101).

pB7 confers kanamycin and chloramphenicol resistance, and contains a cloning site flanked by a BalI site and a HindIII site (Purcell et al., 1983, *Infect Immun* 39:1122–1127).

pACK5 contains the replicon of pAC1 from *Acetobacter pasteurianus* and confers kanamycin resistance (Grones et al., 1995, *Biochem Biophys Res Commun* 206:942–947).

pVAC468 is a suicide vector for chromosomal insertion of heterologous antigens into *Salmonella* and contains a polylinker having the following restriction sites: ClaI, EcoRV, XhoI, SacI, SalI, SmaI, XbaI, and BglII (Hohmann et al., 1995, *Proc Natl Acad Sci USA* 92:2904–2908). Also disclosed is a bacteriophage system, a 'chromosomal expression vector' for inserting genes encoding foreign antigens into the chromosome of *Salmonella*, which uses a defective transposable element carried on bacteriophage lambda (Flynn et al., 1990, *Mol Microb* 4:2111–2118). *Salmonella* can also be made competent (see for example, Purcell et al., 1983, supra) or be electroporated using techniques known to those skilled in the art (see for example, Grones et al., 1995, supra; Coulson et al., 1994, supra).

EXAMPLE 11

Shigella htrB Mutants as Immunogens

In another embodiment, the mutant is a *Shigella* species htrB mutant. Members of the genus *Shigella* are gram-negative bacteria which cause diseases such as dysentery (pathogenic species include dysenteriae, sonnei, and flexneri) primarily in humans. *Shigella* htrB mutants can be produced and identified using the methods according to the present invention, as illustrated in Examples 1–3 and 10. One skilled in the art, using the htrB gene of *H. influenzae*, can isolate the htrB gene of *Shigella*, and produce a mutated htrB gene (unable to encode functional HtrB) using transposon mutagenesis with subsequent recombination resulting in an *Shigella* htrB mutant lacking one or more secondary acyl chains. Alternatively, there may be sufficient homology between *Shigella* and *H. influenzae* to use plasmids pB28 and pB29, each with a mini-Tn3 transposon containing the chloramphenicol acetyl-transferase (CAT) gene inserted into the htrB open reading frame at a different location, to transform *Shigella* for recombination of the mutant htrB gene into the *Shigella* htrB gene. *Shigella* transformants are then selected for by growth in the presence of chloramphenicol (1.5 µg/ml), resulting in identification of *Shigella* htrB mutant strains. Locations of the mTn3 insertion in the chromosomes of the *Shigella* htrB mutants may be confirmed by genomic Southern hybridization using a probe containing htrB sequences. The resultant *Shigella* htrB mutants can then be tested for substantially reduced toxicity using assays described by those skilled in the art for measuring the toxic effects induced by endotoxin.

Using the methods according to the present invention, as illustrated in Examples 4 & 5, endotoxin isolated from an htrB mutant made from a pathogenic *Shigella* species can be used in a vaccine formulation in inducing immunity against the wild type strains of *Shigella*. The htrB mutant LPS may be isolated by a method known to those skilled in the art for isolating LPS. The htrB mutant LPS may be used in a vaccine formulation containing one or more agents selected from the group consisting of a pharmaceutically acceptable carrier (e.g., a physiological solution), an adjuvant, or a carrier protein.

Alternatively, *Shigella* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *Shigella* are known to those skilled in the art, and includes:

pACK5 contains the replicon of PAC1 from *Acetobacter pasteurianus* and confers kanamycin resistance (Grones et al., 1995, supra).

*Shigella* can also be made competent or be electroporated using techniques known to those skilled in the art.

EXAMPLE 12

Pseudomonas aeruginosa htrB Mutants as Immunogens

In another embodiment, the mutant is a *Pseudomonas aeruginosa* htrB mutant. *Pseudomonas aeruginosa* is a gram-negative bacterial pathogen which cause diseases such as respiratory tract infections and sepsis, particularly in immunocompromised patients. Other pathogenic species for humans and animals include *pseudomallei, and mallei*. Mass spectrometry and nuclear magnetic resonance spectroscopy were used to determine the structure of lipid A of *Pseudomonas aeruginosa* LPS. The structure of *P. aeruginosa* lipid A was found to be the same as Enterobacterial lipid A: a backbone of a glucosamine disaccharide which is either mono-phosphorylated or diphosphorylated (positions 1 and 4'); and which carries several molecules of ester- and amide-bound fatty acids. In addition to the hexaacyl and pentaacyl lipid A species, a tetraacyl species was identified (Karunaratne et al., 1992, *Arch Biochem Biophys* 299: 368–76).

*Pseudomonas* htrB mutants (e.g., *P. aeruginosa*) can be produced and identified using the methods according to the present invention, as illustrated in Examples 1–3 and 10. One skilled in the art, using the htrB gene of *H. influenzae*, can isolate the htrB gene of *Pseudomonas aeruginosa*, and produce a mutated htrB gene (unable to encode functional HtrB) using transposon mutagenesis with subsequent recombination resulting in a *P. aeruginosa* htrB mutant lacking one or more secondary acyl chains. Alternatively, there may be sufficient homology between *P. aeruginosa* and *H. influenzae* to use plasmids pB28 and pB29, each with a mini-Tn3 transposon containing the chloramphenicol acetyl-transferase (CAT) gene inserted into the htrB open reading frame at a different location, to transform *P. aeruginosa* for recombination of the mutant htrB gene into the *P. aeruginosa* htrB gene. *P. aeruginosa* transformants are then selected for by growth in the presence of chloramphenicol (1.5 µg/ml), resulting in identification of *P. aeruginosa* htrB mutant strains. Locations of the mTn3 insertion in the chromosomes of the *P. aeruginosa* htrB mutants may be confirmed by genomic Southern hybridization using a probe containing htrB sequences. The resultant *P. aeruginosa* htrB mutants can then be tested for substantially reduced toxicity using assays described by those skilled in the art for measuring the toxic effects induced by endotoxin.

Using the methods according to the present invention, as illustrated in Examples 4 & 5, endotoxin isolated from a *P. aeruginosa* htrB mutant can be used in a vaccine formulation in inducing immunity against the wild type strains of *P. aeruginosa*. The htrB mutant LPS may be isolated by a method known to those skilled in the art for isolating LPS. The htrB mutant LPS may be used in a vaccine formulation containing one or more agents selected from the group consisting of a pharmaceutically acceptable carrier (e.g., a physiological solution), an adjuvant, or a carrier protein.

Alternatively, *P. aeruginosa* htrB mutants can be used in a live bacterial vaccine preparation, in an inactivated bacterial vaccine preparation, and can be genetically engineered to express at least one heterologous bacterial antigen in a multivalent vaccine preparation. Regarding the latter aspect, plasmids useful for cloning of and expression from recombinant DNA molecules into *P. aeruginosa* are known to those skilled in the art, and includes:

pPAH121 confers carbenicillin resistance, and contains a unique HpaI restriction site (Hoyne et al., 1992, *J Bacteriol* 174:7321–7327. *P. aeruginosa* can also be made competent (see for example, Hoyne et al., 1992, supra) or be electroporated using techniques known to those skilled in the art.

EXAMPLE 13

Multivalent htrB Mutant Vaccine Formulation

In one embodiment according to the present invention, as illustrated in Examples 4 & 5, the htrB mutant is genetically engineered to express one or more heterologous microbial antigens in producing a multivalent vaccine using methods known to those skilled in the art. In a preferred embodiment, a microbial pathogen may include a respiratory pathogen selected from the group of pathogens, with respective antigens, in Table 2.

TABLE 2

| PATHOGEN | INFECTION/DISEASE | PROTEIN ANTIGEN |
| --- | --- | --- |
| H. influenzae | otitis media, lower respiratory tract | D-15, P1, P6[1] |
| Group A Streptococcus | pharyngitis, rheumatic fever | M[2] |
| Branhamella catarrhalis | otitis media, lower respiratory tract | CD, E[3] |
| Streptococcus pneumoniae | pneumonia, otitis media, meningitis | autolysin, pneumolysin[4] |
| Bordetella pertussis | pertussis (whooping cough) | filamentous hemagglutinin, pertussis toxin, 69kDa Omp[5] |
| Pseudomonas aeruginosa | respiratory tract | Omp OprF, exotoxin A[6] |
| Legionella pneumophila | pneumonia | OmpS, Hsp60[7] |
| Mycoplasma pneumoniae | upper and lower respiratory tract | P1[8] |
| Respiratory syncytial virus | lower respiratory tract | M2, P, F, G[9] |
| Influenza virus | influenza | HA, M[10] |
| Adenovirus | common cold | |
| rhinovirus | common cold | VP1, VP2, VP3[11] |
| Parainfluenza virus | common cold | HN, F[12] |
| Pneumocystis carinii | pneumonia in AIDS | msg[13] |

[1](Flack et al., 1995 Gene 156:97–99; Panezutti et al., 1993, 61:1867–1872; Nelson et al., 1988, Rev Infect Diseases 10:S331–336).
[2](Pruksakorn et al., 1994, Lancet 344:639–642; Dole et al., 1993, J Immunol 151:2188–94).
[3](Murphy et al., 1989, Infect Immun 57:2938–2941; Faden et al., 1992, Infect Immun 60:3824–3829).
[4](Lock et al., 1992, Microb Pathog 12:137–143).
[5](Novotny et al., 1991, Dev Biol Stand 73:243–249; Lipscombe et al., 1991, Mol Microbiol 5:1385–1392; He et al., 1993, Eur J Clin Microbiol Infect Dis 12:690–695).
[6](Rawling et al., 1995, Infect Immun 63:38–42; Pennington et al., 1988, J Hosp Infect 11A:96–102).
[7](Weeratna et al., 1994, Infect Immun 62:3454–3462).
[8](Jacobs et al., 1990, Infect Immun 58:2464–2469; 1990, J Clin Microbiol 28:1194–1197).
[9](Kulkarni et al., 1995, J Virol 69:1261–1264; Leonov et al., 1994, J Gen Virol 75:1353–1359; Garcia et al., 1993, Virology 195:239–242; Vaux-Peretz et al., 1992, Vaccine 10:113–118).
[10](Kaly et al., 1994, Vaccine 12:753–760; Bucher et al., 1980, J Virol 36:586–590).
[11](Francis et al., 1987, J Gen Virol 68:2687–2691).
[12](Morein et al., 1983, J Gen Virol 64:1557–1569).
[13](Garbe et al., 1994, Infect Immun 62:3092–3101).

In another preferred embodiment, a microbial pathogen may include a pathogen causing a sexually transmitted disease selected from the group of pathogens, with respective antigens, in Table 3.

TABLE 3

| PATHOGEN | INFECTION/DISEASE | PROTEIN ANTIGEN |
| --- | --- | --- |
| N. gonorrhoeae | gonorrhea | IgA1 protease[1], PIB[2], H.8[3], Por[4] |
| Chlamydia trachomatis | nongonococcal urethritis | MOMP[5], HSP[6] |

[1](Lomholt et al., 1994, Infect Immun 62:3178–83).
[2](Heckels et al., 1990, Vaccine 8:225–230).
[3](Blacker et al., 1985, J Infect Dis 151:650–657).
[4](Wetzler et al., 1992, Vaccine 8:225–230).
[5](Campos et al., 1995, Ophthamol Vis Sci 36:1477–91; Murdin et al., 1995, Infect Immun 63:1116–21).
[6](Taylor et al., 1990, Infect Immun 58:3061–3).

Tables 2 & 3, and the references footnoted which are herein incorporated by reference, illustrate various protein antigens, or peptides thereof, viewed by those skilled in the art to be useful as vaccine candidates against the respective microbial pathogen. Typically, the immunopotency of an epitope, whether from a protein or peptide, of a microbial pathogen is determined by monitoring the immune response of an animal following immunization with the epitope and/or by analyzing human convalescent sera in conjunction with pre-immune sera. Thus, one skilled in the art can determine protein or peptide antigens from microbial pathogens which would be desired to include as a heterologous antigen to be expressed by an htrB mutant according to the present invention. A corresponding nucleic acid sequence, the encoding sequence, can then be deduced from the amino acid sequence of the protein or peptide antigen, wherein the encoding sequence is introduced into the htrB mutant for expression.

EXAMPLE 14

Use of htrB Mutants to Generate Antisera

The htrB mutant, or endotoxin purified therefrom, can be used to generate endotoxin-specific antisera, directed to the particular gram-negative bacterial pathogen, which can be used in an immunoassay to detect the antigen (that particular gram-negative bacterial pathogen), present in the body fluid of an individual suspected of having an infection caused by that gram-negative bacterial pathogen. The body fluid(s) collected for analysis depend on the microorganism to be detected, the suspected site of infection, and whether the body fluid is suspected of containing the antigen or containing antisera. With those considerations in mind, the body fluid could include one or more of sputum, blood, cerebrospinal fluid, lesion exudate, swabbed material from the suspected infection site, and fluids from the upper respiratory tract. Immunoassays for such detection comprises any immunoassay known in the art including, but not limited to, radioimmunoassay, ELISA, "sandwich" assay, precipitin reaction, agglutination assay, fluorescent immunoassay, and chemiluminescence-based immunoassay.

Alternatively, where an immunocompromised individual is suffering from a potentially life-threatening infection caused by a particular gram-negative bacterial pathogen, immunization may be passive, i.e. immunization comprising administration of purified human immunoglobulin containing antibody against an htrB mutant or isolated htrB endotosin of that particular gram-negative bacterial pathogen.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

What is claimed is:

1. A method for producing antisera containing antibodies specific to a mutant endotoxin from an htrB mutant non-typeable *Haemophilus influenzae*, the method comprising (a) immunizing an individual with a formulation comprising: (1) an htrB mutant non-typeable *Haemophilus influenzae* having a mutant endotoxin, (2) the mutant endotoxin, or (3) the mutant endotoxin conjugated to a carrier protein, wherein the mutant endotoxin contains a decreased phosphoethanolamine content and an increased hexose content in the mutant endotoxin's inner core, and a pentaaccylated or tetraacylated lipid A lacking one or two secondary acyl chains compared to the corresponding wild-type non-typeable *Haemophilus influenzae* hexaacylated endotoxin, and wherein the mutant endotoxin has substantially reduced toxicity as compared to the wild-type non-typeable *Haemophilus influenzae* hexaacylated endotoxim; and (b) collecting the antisera containing the antibodies from the immunuzed individual.

2. A purified conjugate of a mutant endotoxin from an htrB mutant of non-typeable *Haemophilus influenzae* conjugated to a carrier protein, wherein the mutant endotoxin contains a decreased phosphoethanolamine content and an increased hexose content in the mutant endotoxin's inner core and a pentaacylated or tetraacylated lipid A lacking one or more secondary acyl chains compared to the corresponding wild-type non-typeable *Haemophilus influenzae* hexaacylated endotoxin, and wherein the mutant endotoxin has substantially reduced toxicity as compared to the hexaacylated endotoxin of the wild-type non-typeable *Haemophilus influenzae*.

3. A method for preparing a conjugate of a mutant endotoxin from an htrB mutant of non-typeable *Haemophilus influenzae*, wherein the mutant endotoxin contains a decreased phosphoethanolamine content and an increased hexose content in the mutant endotoxin's inner core and a pentaacylated or tetraacylated lipid A lacking one or more secondary acyl chains compared to the corresponding wild-type non-typeable *Haemophilus influenzae* hexaacylated endotoxin, and wherein the mutant endotoxin has substantially reduced toxicity as compared to the corresponding wild-type non-typeable *Haemophilus influenzae* hexaacylated endotoxin, said method comprising purifying the mutant endotoxin by phenol water extraction or protease digestion and conjugating the purified mutant endotoxin to a carrier protein.

* * * * *

UNITED STATES PATENT AND TRADEMARK OFFICE
CERTIFICATE OF CORRECTION

PATENT NO. : 7,005,129 B1
APPLICATION NO. : 09/077572
DATED : February 28, 2006
INVENTOR(S) : Michael A. Apicella et al.

It is certified that error appears in the above-identified patent and that said Letters Patent is hereby corrected as shown below:

On the cover page, field 57, "htrB" should be italicized, all 4 times it appears.

In column 33, line 56, in claim 1, "htrB" should be italicized.

In column 33, line 59, in claim 1, "htrB" should be italicized.

In column 34, line 58, in claim 1, replace "endotoxim" with --endotoxin--.

In column 34, line 63, in claim 2, "htrB" should be italicized.

In column 35, line 8, in claim 3, "htrB" should be italicized.

Signed and Sealed this

Sixteenth Day of October, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 969
<212> TYPE: DNA
<213> ORGANISM: Haemophilus influenzae, strain 2019
<220> FEATURE:
<221> NAME/KEY: CDS
<222> LOCATION: (34)...(966)

<400> SEQUENCE: 1

```
taaactacgc ccctaactta cgtggaaaga aca atg aaa aac gaa aaa ctc cct        54
                                    Met Lys Asn Glu Lys Leu Pro
                                     1               5 caa ttt caa ccg cac ttt tta gcc cca aaa tac tgg ctt ttt tgg cta       102
Gln Phe Gln Pro His Phe Leu Ala Pro Lys Tyr Trp Leu Phe Trp Leu
         10                  15                  20 ggc gtg gca att tgg cga agt att tta tgt ctt ccc tat cct att ttg       150
Gly Val Ala Ile Trp Arg Ser Ile Leu Cys Leu Pro Tyr Pro Ile Leu
 25                  30                  35 cgc cat att ggt cat ggt ttc ggt tgg ctg ttt tca cat tta aaa gtg       198
Arg His Ile Gly His Gly Phe Gly Trp Leu Phe Ser His Leu Lys Val
 40                  45                  50                  55 ggt aaa cgt cga gct gcc att gca cgc cgt aat ctt gaa ctt tgt ttc       246
Gly Lys Arg Arg Ala Ala Ile Ala Arg Arg Asn Leu Glu Leu Cys Phe
                 60                  65                  70 cct gat atg cct gaa aac gaa cgt gag acg att ttg caa gaa aat ctt       294
Pro Asp Met Pro Glu Asn Glu Arg Glu Thr Ile Leu Gln Glu Asn Leu
             75                  80                  85 cgt tca gta ggc atg gca att atc gaa act ggc atg gct tgg ttt tgg       342
Arg Ser Val Gly Met Ala Ile Ile Glu Thr Gly Met Ala Trp Phe Trp
         90                  95                 100 tcg gat tca cgt atc aaa aaa tgg tcg aaa gtt gaa ggc tta cat tat       390
Ser Asp Ser Arg Ile Lys Lys Trp Ser Lys Val Glu Gly Leu His Tyr
    105                 110                 115 cta aaa gaa aat caa aaa gat gga att gtt ctc gtc ggc gtt cat ttc       438
Leu Lys Glu Asn Gln Lys Asp Gly Ile Val Leu Val Gly Val His Phe
120                 125                 130                 135 tta acg cta gaa ctt ggc gca cgc atc att ggt tta cat cat cct ggc       486
Leu Thr Leu Glu Leu Gly Ala Arg Ile Ile Gly Leu His His Pro Gly
                140                 145                 150 att ggt gtt tat cgt cca aat gat aat cct ttg ctt gat tgg cta caa       534
Ile Gly Val Tyr Arg Pro Asn Asp Asn Pro Leu Leu Asp Trp Leu Gln
            155                 160                 165 aca caa ggc cgt tta cgc tcc aat aaa gat atg ctt gat cgt aaa gat       582
Thr Gln Gly Arg Leu Arg Ser Asn Lys Asp Met Leu Asp Arg Lys Asp
        170                 175                 180 tta cgc gga atg atc aaa gct tta cgc cac gaa gaa acc att tgg tat       630
Leu Arg Gly Met Ile Lys Ala Leu Arg His Glu Glu Thr Ile Trp Tyr
    185                 190                 195 gcg cct gat cac gat tac ggc aga aaa aat gcc gtt ttt gtt cct ttt       678
Ala Pro Asp His Asp Tyr Gly Arg Lys Asn Ala Val Phe Val Pro Phe
200                 205                 210                 215 ttt gca gta cct gac act tgc act act act ggt agt tat tat tta ttg       726
Phe Ala Val Pro Asp Thr Cys Thr Thr Thr Gly Ser Tyr Tyr Leu Leu
                220                 225                 230 aaa tcc tcg caa aac agc aaa gtg att cca ttt gcg cca tta cgc aat       774
Lys Ser Ser Gln Asn Ser Lys Val Ile Pro Phe Ala Pro Leu Arg Asn
            235                 240                 245
```

-continued

```
aaa gat ggt tca ggc tat acc gtg agc att tca gcg cct gtt gat ttt      822
Lys Asp Gly Ser Gly Tyr Thr Val Ser Ile Ser Ala Pro Val Asp Phe
            250                 255                 260 aca gat tta caa gat gaa gta gcg ata gct gtg cga atg aat caa atc      870
Thr Asp Leu Gln Asp Glu Val Ala Ile Ala Val Arg Met Asn Gln Ile
            265                 270                 275 gtt gaa aag gaa atc atg aag ggc ata tca caa tat atg tgg cta cat      918
Val Glu Lys Glu Ile Met Lys Gly Ile Ser Gln Tyr Met Trp Leu His
280                 285                 290                 295 cgt cgt ttt aaa aca cgc ccc gat gaa aat acg cct agt tta tac gat      966
Arg Arg Phe Lys Thr Arg Pro Asp Glu Asn Thr Pro Ser Leu Tyr Asp
                300                 305                 310 taa                                                                  969
```

<210> SEQ ID NO 2
<211> LENGTH: 31
<212> TYPE: DNA
<213> ORGANISM: Haemophilus influenzae, strain 2019

<400> SEQUENCE: 2
ccaatatggc gcaaaatagg atagggaaga c                                    31

<210> SEQ ID NO 3
<211> LENGTH: 9
<212> TYPE: DNA
<213> ORGANISM: Unknown
<220> FEATURE:
<223> OTHER INFORMATION: An uptake sequence involved in a transformation
      process for H. influenzae.

<400> SEQUENCE: 3 aagtgcggt                                                              9

<210> SEQ ID NO 4
<211> LENGTH: 30
<212> TYPE: DNA
<213> ORGANISM: Homo sapiens

<400> SEQUENCE: 4
atctctcagc tccacgccat tggccaggag                                      30

<210> SEQ ID NO 5
<211> LENGTH: 30
<212> TYPE: DNA
<213> ORGANISM: Homo sapiens

<400> SEQUENCE: 5
ctcctggcca atggcgtgga gctgagagat                                      30